(12) United States Patent
Mukumoto

(10) Patent No.: US 8,152,744 B2
(45) Date of Patent: Apr. 10, 2012

(54) SHOE OR INSOLE FITTING NAVIGATION SYSTEM

(75) Inventor: Mitsuru Mukumoto, Osaka (JP)

(73) Assignee: Comfort Lab. Inc., Osaka (JP)

( * ) Notice: Subject to any disclaimer, the term of this patent is extended or adjusted under 35 U.S.C. 154(b) by 205 days.

(21) Appl. No.: 12/382,650

(22) Filed: Mar. 20, 2009

(65) Prior Publication Data

US 2009/0247909 A1    Oct. 1, 2009

(30) Foreign Application Priority Data

Mar. 25, 2008  (JP) ................. 2008-078698

(51) Int. Cl.
  *A61B 5/103* (2006.01)
  *A61B 5/117* (2006.01)
(52) U.S. Cl. ...................... 600/592; 600/587
(58) Field of Classification Search .......... 600/592; 702/150
  See application file for complete search history.

(56) References Cited

U.S. PATENT DOCUMENTS

| | | | | |
|---|---|---|---|---|
| 5,164,793 A | * | 11/1992 | Wolfersberger et al. | 356/607 |
| 5,388,591 A | * | 2/1995 | De Luca et al. | 600/592 |
| 5,753,931 A | * | 5/1998 | Borchers et al. | 250/559.22 |
| 5,790,256 A | * | 8/1998 | Brown et al. | 356/613 |
| 5,979,067 A | * | 11/1999 | Waters | 33/512 |
| 2008/0188775 A1 | * | 8/2008 | Schneider | 600/592 |

FOREIGN PATENT DOCUMENTS

| | | |
|---|---|---|
| JP | 2001-275716 A | 10/2001 |
| JP | 2004-000786 A | 1/2004 |
| JP | 2004-219404 A | 8/2004 |
| JP | 2004-305374 A | 11/2004 |
| JP | 2006-141651 A | 6/2006 |

* cited by examiner

*Primary Examiner* — Max Hindenburg
*Assistant Examiner* — Charles Becker
(74) *Attorney, Agent, or Firm* — Rabin & Berdo, PC

(57) ABSTRACT

The present invention presents a shoe or insole fitting navigation system including a set of foot sole pressure measuring sensors for measuring foot sole pressure distributions; a set of TV cameras for taking foot images; a processor; and a monitor screen. The present system acquires right and left foot sole pressure data, acquires right and left foot images, computes a foot sole gravity center position of each foot, computes an outer dimension of each foot, and determines bias in gravity center balance of each foot accurately based on the foot sole gravity center position of each foot and the outer dimension of each foot. In addition, the present system determines an abnormal foot symptom of each foot, and selects a shoe or insole of each foot based on the determined bias in gravity center balance and the determined foot symptom.

22 Claims, 16 Drawing Sheets

Gravity center balance determination division diagram

FIG. 8
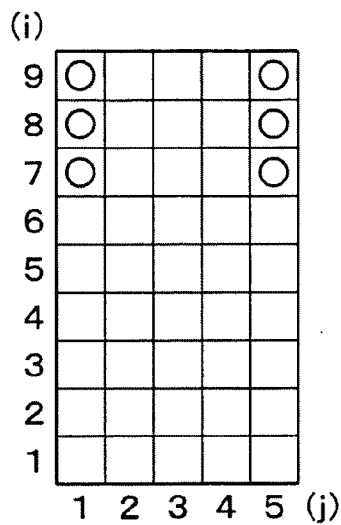
(1) Front foot part problem determination 1
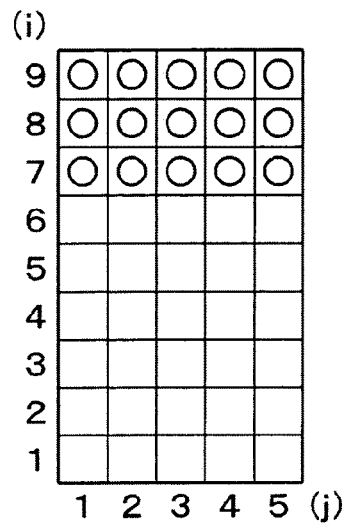
(2) Front foot part problem determination 2
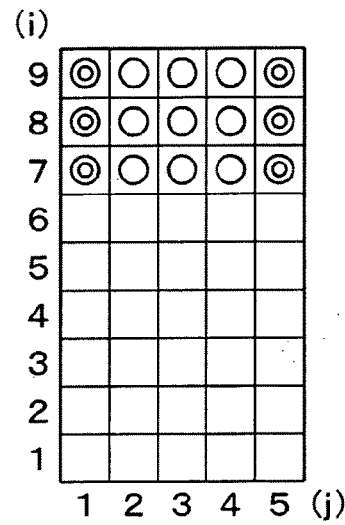
(3) Front foot part problem determination 3
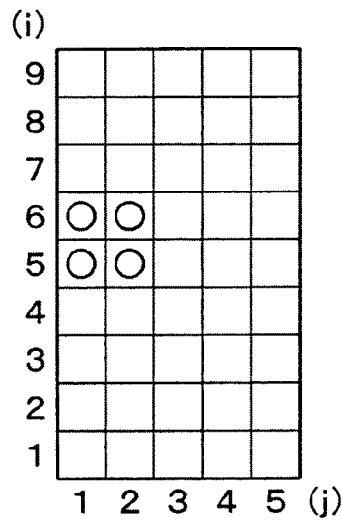
(4) Flat foot determination
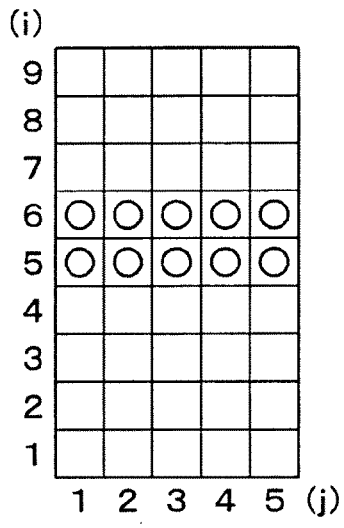
(5) High arch determination
Foot symptom determination division diagram

FIG. 10

Insole selection table part (1)

| No. | Gravity center balance determination flag | | | | Symptom determination flag | | | Foot diagnosis message No. | Insole selection message No. | Insole No. |
|---|---|---|---|---|---|---|---|---|---|---|
| | Front (F) | Rear (R) | Inside (I) | Outside (O) | Front foot part (FP) | Flat foot (FF) | High arch (HA) | | | |
| 1 | 0 | 0 | 0 | 0 | 0 | 0 | 0 | 10 | 30 | — |
| 2 | 1 | 0 | 0 | 0 | 0 | 0 | 0 | 11 | 31 | 1 |
| 3 | 0 | 1 | 0 | 0 | 0 | 0 | 0 | 12 | 31 | 2 |
| 4 | 0 | 0 | 1 | 0 | 0 | 0 | 0 | 13 | 31 | 3 |
| 5 | 0 | 0 | 0 | 1 | 0 | 0 | 0 | 14 | 31 | 4 |
| 6 | 1 | 0 | 1 | 0 | 0 | 0 | 0 | 15 | 31 | 8 |
| 7 | 1 | 0 | 0 | 1 | 0 | 0 | 0 | 16 | 31 | 9 |
| 8 | 0 | 1 | 1 | 0 | 0 | 0 | 0 | 17 | 31 | 3 |
| 9 | 0 | 1 | 0 | 1 | 0 | 0 | 0 | 18 | 31 | 4 |
| 10 | 0 | 0 | 0 | 0 | 1 | 0 | 0 | 21 | 32 | 1 |
| 11 | 1 | 0 | 0 | 0 | 1 | 0 | 0 | 11, 21 | 33 | 1 |
| 12 | 0 | 1 | 0 | 0 | 1 | 0 | 0 | 12, 21 | 34 | 10, 2 |
| 13 | 0 | 0 | 1 | 0 | 1 | 0 | 0 | 13, 21 | 33 | 8 |
| 14 | 0 | 0 | 0 | 1 | 1 | 0 | 0 | 14, 21 | 33 | 9 |
| 15 | 1 | 0 | 1 | 0 | 1 | 0 | 0 | 15, 21 | 33 | 8 |
| 16 | 1 | 0 | 0 | 1 | 1 | 0 | 0 | 16, 21 | 33 | 9 |
| 17 | 0 | 1 | 1 | 0 | 1 | 0 | 0 | 17, 21 | 34 | 8, 3 |
| 18 | 0 | 1 | 0 | 1 | 1 | 0 | 0 | 18, 21 | 34 | 9, 4 |
| 19 | 0 | 0 | 0 | 0 | 0 | 1 | 0 | 22 | 35 | 6 |
| 20 | 1 | 0 | 0 | 0 | 0 | 1 | 0 | 11, 22 | 36 | 7 |
| 21 | 0 | 1 | 0 | 0 | 0 | 1 | 0 | 12, 22 | 36 | 16 |
| 22 | 0 | 0 | 1 | 0 | 0 | 1 | 0 | 13, 22 | 36 | 14 |
| 23 | 0 | 0 | 0 | 1 | 0 | 1 | 0 | 14, 22 | 36 | 15 |
| 24 | 1 | 0 | 1 | 0 | 0 | 1 | 0 | 15, 22 | 36 | 11 |
| 25 | 1 | 0 | 0 | 1 | 0 | 1 | 0 | 16, 22 | 36 | 12 |
| 26 | 0 | 1 | 1 | 0 | 0 | 1 | 0 | 17, 22 | 36 | 14 |
| 27 | 0 | 1 | 0 | 1 | 0 | 1 | 0 | 18, 22 | 36 | 15 |

FIG. 11

Insole selection table part (2)

| No. | Gravity center balance determination flag | | | | Symptom determination flag | | | Foot diagnosis message No. | Insole selection message No. | Insole No. |
|---|---|---|---|---|---|---|---|---|---|---|
| | Front (F) | Rear (R) | Inside (I) | Outside (O) | Front foot part (FP) | Flat foot (FF) | High arch (HA) | | | |
| 28 | 0 | 0 | 0 | 0 | 1 | 1 | 0 | 23 | 37 | 7 |
| 29 | 1 | 0 | 0 | 0 | 1 | 1 | 0 | 11, 23 | 38 | 7 |
| 30 | 0 | 1 | 0 | 0 | 1 | 1 | 0 | 12, 23 | 39 | 7, 16 |
| 31 | 0 | 0 | 1 | 0 | 1 | 1 | 0 | 13, 23 | 38 | 11 |
| 32 | 0 | 0 | 0 | 1 | 1 | 1 | 0 | 14, 23 | 38 | 12 |
| 33 | 1 | 0 | 1 | 0 | 1 | 1 | 0 | 15, 23 | 38 | 11 |
| 34 | 1 | 0 | 0 | 1 | 1 | 1 | 0 | 16, 23 | 38 | 12 |
| 35 | 0 | 1 | 1 | 0 | 1 | 1 | 0 | 17, 23 | 39 | 11, 14 |
| 36 | 0 | 1 | 0 | 1 | 1 | 1 | 0 | 18, 23 | 39 | 12, 15 |
| 37 | 0 | 0 | 0 | 0 | 0 | 0 | 1 | 24 | 40 | 7 |
| 38 | 1 | 0 | 0 | 0 | 0 | 0 | 1 | 11, 24 | 41 | 7 |
| 39 | 0 | 1 | 0 | 0 | 0 | 0 | 1 | 12, 24 | 41 | 13 |
| 40 | 0 | 0 | 1 | 0 | 0 | 0 | 1 | 13, 24 | 41 | 11 |
| 41 | 0 | 0 | 0 | 1 | 0 | 0 | 1 | 14, 24 | 41 | 12 |
| 42 | 1 | 0 | 1 | 0 | 0 | 0 | 1 | 15, 24 | 41 | 11 |
| 43 | 1 | 0 | 0 | 1 | 0 | 0 | 1 | 16, 24 | 41 | 12 |
| 44 | 0 | 1 | 1 | 0 | 0 | 0 | 1 | 17, 24 | 41 | 11 |
| 45 | 0 | 1 | 0 | 1 | 0 | 0 | 1 | 18, 24 | 41 | 12 |
| 46 | 0 | 0 | 0 | 0 | 1 | 0 | 1 | 25 | 42 | 7 |
| 47 | 1 | 0 | 0 | 0 | 1 | 0 | 1 | 11, 25 | 43 | 7 |
| 48 | 0 | 1 | 0 | 0 | 1 | 0 | 1 | 12, 25 | 44 | 7, 13 |
| 49 | 0 | 0 | 1 | 0 | 1 | 0 | 1 | 13, 25 | 43 | 11 |
| 50 | 0 | 0 | 0 | 1 | 1 | 0 | 1 | 14, 25 | 43 | 12 |
| 51 | 1 | 0 | 1 | 0 | 1 | 0 | 1 | 15, 25 | 43 | 11 |
| 52 | 1 | 0 | 0 | 1 | 1 | 0 | 1 | 16, 25 | 43 | 12 |
| 53 | 0 | 1 | 1 | 0 | 1 | 0 | 1 | 17, 25 | 44 | 7, 14 |
| 54 | 0 | 1 | 0 | 1 | 1 | 0 | 1 | 18, 25 | 44 | 7, 15 |

FIG. 12

Foot diagnosis message table

| No. | Foot diagnosis message |
|---|---|
| 10 | No particular problem is found |
| 11 | Gravity center is biased to the front side |
| 12 | Gravity center is biased to the rear side |
| 13 | Gravity center is biased to the inside |
| 14 | Gravity center is biased to the outside |
| 15 | Gravity center is biased to the front side and inside |
| 16 | Gravity center is biased to the front side and outside |
| 17 | Gravity center is biased to the rear side and inside |
| 18 | Gravity center is biased to the rear side and outside |
| 21 | Front foot part may have a trouble |
| 22 | Foot may be flat |
| 23 | Front foot part may have a trouble and foot may be flat |
| 24 | Foot may have a high arch |
| 25 | Front foot part may have a trouble and foot may have a high arch |

FIG. 13

Insole selection message table

| No. | Insole selection message |
|---|---|
| 30 | Standard type of insoles is recommended |
| 31 | This type of insoles is recommended to move gravity center biased to the center side |
| 32 | This type of insoles is recommended to care front foot part |
| 33 | This type of insoles is recommended to care front foot part and to move gravity center to the center side |
| 34 | In the case of trouble with front foot part, the former type of insoles is recommended to care front foot part |
| 34 | In the case of no trouble with front foot part, the latter type of insoles is recommended to move gravity center to the center side |
| 35 | This type of insoles is recommended to care flat foot |
| 36 | This type of insoles is recommended to care flat foot and move gravity center to the center side |
| 37 | This type of insoles is recommended to care front foot part and flat foot |
| 38 | This type of insoles is recommended to care front foot part and flat foot and to move gravity center to the center side |
| 39 | In the case of trouble with front foot part, the former type of insoles is recommended to care front foot part and flat foot |
| 39 | In the case of no trouble with front foot part, the latter type of insoles is recommended to care flat foot and to move gravity center to the center side |
| 40 | This type of insoles is recommended to care high arch |
| 41 | This type of insoles is recommended to care high arch and to move gravity center to the center side |
| 42 | This type of insoles is recommended to care front foot part and high arch |
| 43 | This type of insoles is recommended to care front foot part and high arch and to move gravity center to the center side |
| 44 | In the case of trouble with front foot part, the former type of insoles is recommended to care front foot part and high arch |
| 44 | In the case of no trouble with front foot part, the latter type of insoles is recommended to care high arch and to move gravity center to the center side |

SHOE OR INSOLE FITTING NAVIGATION SYSTEM

BACKGROUND OF THE INVENTION

1. Technical Field of the Invention

The present invention relates to a system for navigating shoe or insole selection, more particularly to a shoe or insole fitting navigation system capable of adequately navigating selection of foot-problem-care shoes or insoles.

2. Description of Related Art

The human being realizes walking on his/her two legs by shifting his/her gravity centers while skillfully controlling his/her joints and muscles. However, different people have different foot shapes and walking postures. When a person is walking while gravity center balance remains biased or while a problem such as hallux valgus, a flat foot, or a high arch is present, problems such as falling accident during walking or health impairment due to excessive load imposed on feet or lower limbs may be caused.

Therefore, it has been conventionally practiced that those having a foot problem improve these problems by fitting foot-problem-care shoes or insoles.

However, fitting of such foot-problem-care shoes or insoles has required diagnoses by an expert such as a shoe fitter who can adequately diagnose foot condition and posture, and it has been difficult to select adequate foot-problem-care shoes or insoles in shops without such experts.

According to the above situation, a navigation system capable of adequately selecting foot-problem-care shoes or insoles even in shops without such experts has been expected.

As conventional art for automatically selecting foot-problem-care shoes or insoles, for example, the following patent references have been disclosed.

Patent reference 1 discloses technology of measuring an inclination angle and an arch height rate of a foot by a foot-print measuring device and then selecting a shoe or shoe part by referring a table where relationship of inclination angles and arch height rates of foot with shoe types is defined.

Patent reference 2 discloses technology of measuring a three-dimensional foot shape, obtaining an anteroposterior two-dimensional cross section including a heel cross section from the measured three-dimensional shape, and obtaining an inclination angle from a center line of the two-dimensional cross section, and selecting a shoe or shoe insole that corrects the inclination to inside or outside of the feet.

Patent reference 3 discloses technology of taking a foot sole print by using coloration liquid and coloration paper, reading the taken foot sole print into a computer with an image scanner, and selecting insoles by referring a table where foot information and insole information are associated with each other previously.

Patent reference 4 discloses technology of taking images of feet placed on a transparent footrest plate from the rear side, introducing first light from the outer-circumferential-side end face of the transparent footrest plate and irradiating the outer circumferential side surfaces of the feet with second light of a color different from that of the first light to thereby simultaneously measure a shape of ground surface of the foot sole and an outer circumferential shape of the foot sole.

Patent reference 5 discloses technology of measuring foot sole pressure distribution and introducing shoes in which the foot sole pressure is averagely dispersed.

Patent reference 1: Japanese Patent Application Laid-Open Publication No. 2006-141651

Patent reference 2: Japanese Patent Application Laid-Open Publication No. 2004-000786

Patent reference 3: Japanese Patent Application Laid-Open Publication No. 2004-305374

Patent reference 4: Japanese Patent Application Laid-Open Publication No. 2004-219404

Patent reference 5: Japanese Patent Application Laid-Open Publication No. 2001-275716

However, Patent references 1 and 2, where shoes or insoles are selected based on the foot shape only, have raised a problem that shoes or insoles appropriately caring a foot problem cannot be selected adequately since load imposed on soles varies depending on posture of an upper body.

Moreover, Patent reference 3, where shoes or insoles are selected based on the foot sole print, has raised the problem that shoes or insoles appropriately caring a foot problem cannot be selected adequately since the load actually imposed on the soles cannot be judged from the foot sole print.

Moreover, Patent reference 4, where the shape of the ground surface of the foot sole and the outer circumferential shape of the foot sole are simultaneously measured, has also raised the problem that shoes or insoles appropriately caring a foot problem cannot be selected adequately since the actual load imposed on the foot soles cannot be judged.

On the other hand, Patent reference 5, where it is possible to select shoes or insoles based on the load imposed on the foot soles since the foot sole pressure distribution is measured, raises a case where, in the measurement of the foot sole pressure, the foot sole pressure distribution may have a defect part where the load can not be measured, for example, in a toe part or any troubled part. In such a case, even when the load center is obtained from the measured foot sole pressure distribution, the gravity center position in the entire foot sole can not be correctly recognized. Therefore, there has arisen a problem that only measuring the foot sole pressure can not determine bias in gravity center balance of a foot sole accurately, thus making it difficult to select shoes or insoles appropriately caring a foot problem.

SUMMARY OF THE INVENTION

The present invention has been made to solve the problems described above, and an object of the present invention is to detect bias in gravity center balance of foot sole accurately anytime and to select foot-care shoes or insoles adequately.

A preferred embodiment according to the present invention provides a shoe or insole fitting navigation system which includes a foot sole pressure measuring sensor configured to measure a foot sole pressure distribution for each foot of a subject standing upright on a measuring plane, an outer foot dimension measuring sensor configured to measure an outer dimension of each foot of the subject by detecting an outer position of each foot, a gravity center position computing section configured to compute a gravity center position of each foot on the basis of the outer position of each foot detected by the outer foot dimension measuring sensor from the foot sole pressure distribution of each foot measured by the foot sole pressure measuring sensor, a gravity center balance determining section configured to determine bias in gravity center balance of each foot which represents how much the gravity center position is biased from a central portion of foot sole based on the gravity center position of each foot computed by the gravity center position computing section and the outer dimension of each foot measured by the outer foot dimension measuring sensor, and a selecting section configured to select a foot-problem-care shoe or insole of each foot based on the bias in gravity center balance of each foot determined by the gravity center balance determining section.

According to this preferred embodiment, since the foot sole pressure measuring sensor measures the foot sole pressure distribution of each foot of the subject standing upright on a measuring plane and also the outer foot dimension measuring sensor measures the outer dimension of each foot, foot sizes and foot sole pressure distributions of the subject can be measured simultaneously.

In addition, since the gravity center position computing section computes the gravity center position of each foot on the basis of the outer position of each foot detected by the outer foot dimension measuring sensor from the foot sole pressure distribution of each foot measured by the foot sole pressure measuring sensor, even when part of the foot sole has a defect part where load is not measured in the foot sole pressure distribution measured by the foot sole pressure measuring sensor, the gravity center position on an entire foot sole can be correctly recognized. And since the gravity center balance determining section determines the bias in gravity center balance based on the computed gravity center position of each foot and the measured outer dimension of each foot, the bias in gravity center balance can be always determined accurately, thus permitting adequate selection of a foot-problem-care shoe or insole.

Here, the gravity center position computing section may compute a gravity center position of each foot by extracting an pressure distribution of foot sole part of each foot from the foot sole pressure distribution of each foot measured by the foot sole pressure measuring sensor based on the outer position of each foot detected by the outer foot dimension measuring sensor and computing the gravity center position of each foot based on the extracted pressure distribution of foot sole part of each foot.

Note that the gravity center position computing section may compute the gravity center position of each foot from the entire foot sole pressure distribution of each foot measured by each of the foot sole pressure measuring sensor, and the gravity center balance determining section may determine the bias in gravity center balance of each foot based on the gravity center position of each foot computed by the gravity center position computing section and the outer position of each foot detected by the outer foot dimension measuring sensor, which is same as the preferred embodiment of the present invention substantially.

Also note that "foot sizes and foot sole pressure distributions of the subject can be measured simultaneously" only requires performing both of the measurement of the foot sole pressure distributions and the measurement of the outer dimensions of the feet in the gravity center balance determination made for the same subject, and thus is not necessarily limited to performing the measurement of the foot sole pressure and the measurement of the outer dimensions of the feet at the same time.

An another preferred embodiment according to the present invention provides a shoe or insole fitting navigation system which includes a foot sole pressure measuring sensor configured to measure a foot sole pressure distribution of each foot of a subject standing upright on a measuring plane, an outer foot dimension measuring sensor configured to measure an outer dimension of each foot of the subject, an outer foot position estimating section configured to estimate an outer position of each foot by extracting a region of each foot where the pressure is detected from the foot sole pressure distribution measured by the foot sole pressure measuring sensor, determining reference positions in a direction of front and rear and in a direction of inside and outside of each foot based on the foot sole pressure distribution of the extracted region of each foot, and setting an outer foot frame of each foot corresponding to the outer dimension of each foot measured by the outer foot dimension measuring sensor to the determined reference positions of each foot, a gravity center position computing section configured to compute a gravity center position of each foot on the basis of the outer foot position of each foot estimated by the outer foot position estimating section from the foot sole pressure distribution measured by the foot sole pressure measuring sensors, a gravity center balance determining section configured to determine bias in gravity center balance of each foot which represents how much the gravity center position is biased from a central portion of the foot sole based on the gravity center position of each foot computed by the gravity center position computing section and the outer dimension of each foot measured by the outer foot dimension measuring sensor, and a selecting section configured to select a foot-problem-care shoe or insole based on the bias in gravity center balance of each foot determined by the gravity center balance determining section.

According to this preferred embodiment, since the outer foot position estimating section estimates the outer position of each foot based on the foot sole pressure distribution measured by the foot sole pressure measuring sensor, corresponding to the outer dimension of each foot measured by the outer foot dimension measuring sensor, and the gravity center balance determining section computes the gravity center position of each foot on the basis of the outer position of each foot estimated by the outer foot position estimating section from the foot sole pressure distribution measured by the foot sole pressure measuring sensor, even when part of the foot sole has a defect part where load is not measured in the foot sole pressure distribution measured by the foot sole pressure measuring sensor, the gravity center position on the entire foot sole can be correctly recognized.

And since the gravity center balance determining section determines the bias in gravity center balance of each foot based on the computed gravity center position of each foot and the outer dimension of each foot measured by the outer foot dimension measuring section, the bias in gravity center balance can be always determined accurately, thus permitting adequate selection of a foot-problem-care shoe or insole.

Note that the gravity center computing section may compute the gravity center position of each foot from the entire foot sole pressure distribution measured by the foot sole pressure measuring sensor, and the gravity center balance determining section may determine the bias in gravity center balance of each foot based on the gravity center position of each foot computed by the gravity center position computing section and the outer position of each foot estimated by the outer foot position estimating unit, which is same as the preferred embodiment of the present invention substantially.

The outer foot dimension measuring sensor may preferably include an image taking TV camera configured to take a foot image of each foot, and image processing section configured to compute a foot length and a foot width by detecting the an outer position of each foot from the foot image of each foot taken by the image taking TV camera.

According to this preferred embodiment, since the image taking TV camera takes the foot image of each foot and the image processing section computes the foot length and the foot width of each foot by detecting the outer position of each foot, the subject can measure the foot sizes and the foot sole pressure distributions simultaneously only by standing upright on the measuring plane of the foot sole pressure measuring sensor.

The foot sole pressure measuring sensor may include a heel stopper of each foot for adjusting the subject's heel to a reference position, the image taking TV camera may take a foot image of each foot from upper front direction, and the image processing section may detect frontmost position of foot, innermost position of foot and outermost position of foot, and computes a foot length based on the detected frontmost position of foot and the position of the heel stopper, and computes a foot width based on the detected innermost position of foot and the detected outermost position of foot, for each foot.

The shoe or insole fitting navigation system according to the preferred embodiment of the present invention may preferably further include foot symptom determining section configured to determine whether or not an abnormal foot symptom is existing in each foot, by dividing the foot sole pressure distribution of each foot measured by the foot sole pressure measuring sensor into a plurality of regions, computing pressure class values in these divided regions, and comparing the computed pressure class values with previously defined combination condition of pressure class values, whereby the selecting section may select a foot-care shoe or insole based not only on the bias in gravity center balance of each foot determined by the gravity center balance determining section but also on the foot symptom of each foot determined by the foot symptom determining section.

According to this preferred embodiment, since the foot symptom determining section divides the foot sole pressure distribution measured by the foot sole pressure measuring sensor into a plurality of regions and determines whether or not an abnormal foot symptom is existing based on the combination of the pressure class values computed for each of the regions, and the selecting section selects a foot-problem-care shoe or insole based on not only the bias in gravity center balance determined by the gravity center balance determining section but also the foot symptom determined by the foot symptom determining section, appropriate shoes or insoles can be selected even for a subject having an abnormal foot symptom.

The foot symptom determining section may be configured to divide a foot sole region excluding a toe part into a plurality of regions and compute pressure class values in these divided regions, determine whether or not a front foot part problem including a hallux valgus is existing by comparing the computed pressure class values in a front foot part with previously defined combination condition of pressure class values, determine whether or not a flat foot is existing by comparing the computed pressure class values in an inside part of middle foot part with predetermined combination condition of pressure class values, and determine whether or not a high arch is existing by comparing the computed pressure class values in an entire middle foot part with predetermined combination condition of pressure class values.

According to this preferred embodiment, since the foot sole region excluding a toe part is divided into a plurality of regions, the front foot part problem including hallux valgus is determined based on the combination of the pressure class values in a front foot part, a flat foot is determined based on the combination of the pressure class values in an inside part of middle foot part, and a high arch is determined based on the combination of the pressure class values in an entire middle foot part, a shoe or insole can be selected which can appropriately care the front foot part problems including hallux valgus, a flat foot, and a high arch when the subject has any of these problems.

The selecting section may be configured to select a shoe or insole by combining the selection of a shoe or insole for improving the bias in gravity center balance determined by the gravity center balance determining section with the selection of a shoe or insole for improving the foot symptom determined by the foot symptom determining section, and when the selection based on the gravity center balance determining section conflicts with the selection based on the foot symptom determining section, priority is given to the selection based on the foot symptom determining section.

According to this preferred embodiment, since priority is given to the selection based on the foot symptom determining section when the selection based on the gravity center balance determining section conflicts with the selection based on the foot symptom determining section, an appropriate shoe or insole without excessive load imposed on the serious foot symptom can be recommended to the subject.

The selecting section may be configured to present an alignment method of one or more pads to a shoe or insole.

According to this preferred embodiment, since the alignment method of one or more pads is presented for improving the determined bias in gravity center balance and/or the determined foot symptom, a customer-made shoe or insole which improves the foot problem can be provided.

The shoe or insole fitting navigation system according to the preferred embodiment of the present invention may further include gravity center fluctuation computing section configured to compute fluctuation of gravity center of each foot based on change of the gravity center position of each foot computed by the gravity center position computing section within a given period of time, whereby suitability of the selected shoe or insole can be evaluated by measuring the fluctuation of gravity center of each foot when the subject wears the shoe or insole selected by the selecting section.

According to this preferred embodiment, the gravity center fluctuation of each foot can be obtained from the foot sole pressure distribution of each foot measured by the foot sole pressure measuring sensor, and the gravity center fluctuation when the subject wears the selected shoe or insole can be measured to thereby evaluate the suitability of the selected shoe or insole. Accordingly, the foot-care shoe or insole can be more adequately selected.

In addition, a plurality of candidate types of shoe or insole may be selected by the selecting section, and the optimal type of shoe or insole may be determined by measuring the gravity center fluctuation when the subject wears each of the selected types of shoe or insole.

The shoe or insole fitting navigation system according to the present invention may further include a pelvis diagnosis section configured to diagnose a pelvis condition of the subject by combining the determination result of the bias in gravity center balance of the left foot and that of the right foot, wherein a related pelvis diagnosis message is extracted based on the determination results of the bias in gravity center balance of both feet determined by the gravity center balance determining section by referring to a pelvis diagnosis table in which pelvis diagnosis messages describing pelvis diagnosis information corresponding to a combination of a determination result of the bias in gravity center balance of the left foot and that of the right foot are registered, to display the extracted pelvis diagnosis message on a screen.

According to this preferred embodiment, the subject's pelvis condition can be diagnosed by combining the determination results of the bias in gravity center of both feet determined by the gravity center balance determining section.

Based on result of this diagnosis, the shoe or insole selection can be modified to thereby select shoe or insole more adequately caring a subject's foot problem.

In addition, based on the result of this diagnosis, advice from a doctor for improving the pelvis problem can be presented to thereby more appropriately care the subject's foot problem.

The determination result provided by the foot symptom determining section may also be combined to diagnose the subject's pelvis condition.

The shoe or insole fitting navigation system according to the present invention may further include a posture simulation displaying section configured to display a posture simulation by generating a three-dimensional human body model of the subject based on body information of the subject, deforming the generated three-dimensional human body model based on the bias in gravity center balance of both feet determined by the gravity center balance determining section, and displaying the deformed three-dimensional human body model on a screen.

According to this preferred embodiment, since the subject's three-dimensional human body model deformed based on the bias in gravity center balance of both feet determined by the gravity center balance determining section is displayed on the screen, the subject can visually recognize how the bias in gravity center balance of the feet affects the entire body.

The three-dimensional human body model of the subject may be generated by deforming a standard three-dimensional human body model based on the body information of the subject (for example, height, weight, gender, age, chest measurement, waist measurement, and hip measurement), or by selecting, based on the body information of the subject, from among a plurality of three-dimensional human body models previously prepared.

The deformation of the three-dimensional human body model based on the bias in gravity center balance of both feet can be performed by, for example, referring to a posture deformation table defining how and which part of the three-dimensional human body model is deformed for the determined bias in gravity center balance of each foot.

The body information of the subject may be inputted by the subject, may be automatically measured by detecting features from an image taken with a digital camera, or may be automatically inputted by an automatic measurement technology used in an apparel field and other fields.

The posture simulation displaying section may include a moment computing section which is configured to compute a total load imposed on the gravity center of each foot based on the foot sole pressure distribution of each foot measured by the foot sole pressure measuring sensor, compute a total gravity center position and total load of both feet based on the computed gravity center positions of each foot and the computed total load of each foot, compute an ideal gravity center position based on the outer positions of the subject's both feet, and compute a moment working on the subject's body based on the computed total gravity center position, the computed total load of both feet and the computed ideal gravity center position, whereby deforming the generated subject's three-dimensional human body model based on the computed moment and displaying the deformed three-dimensional human body model on the screen.

According to this preferred embodiment, since the moment that works on the subject's body due to the bias in gravity center balance is computed and the subject's three-dimensional human body model deformed based on the computed moment is displayed on the screen, the subject can visually confirm how the moment caused by the bias in gravity center balance acts on his/her own body.

The deformation of the three-dimensional human body model based on the computed moment can be performed by, for example, referring to the posture deformation table defining how and which part of the three-dimensional human body model is deformed for the moment.

As described above, the present invention provides advantage that bias in gravity center balance of foot sole can be always determined accurately, and a foot-problem-care shoe or insole can be selected adequately.

Note that the shoe or insole selected by the shoe or insole fitting navigation system of the present invention includes any kind of foot-care goods, leg-care goods, leg clothes and the like such as socks or supporters for care of foot problems used along with shoes or insoles.

The aforementioned objects, other objects, features, and advantages of the present invention will be further clarified by the following detailed description of the preferred embodiment with reference to the accompanying drawings.

BRIEF DESCRIPTION OF THE DRAWINGS

FIG. 8 shows determination division of the foot symptom determining processing in the insole selection navigation processing according to the preferred embodiment of the present invention (for a right foot);

FIG. 10 is an example of an insole selection table (Part 1) for selecting an insole in the insole selection navigation processing;

FIG. 11 is an example of the insole selection table (Part 2) for selecting an insole in the insole selection navigation processing;

FIG. 12 is an example of a message table for displaying a foot diagnosis message in the insole selection navigation processing;

FIG. 13 is an example of a message table for displaying an insole selection message in the insole selection navigation processing;

DETAILED DESCRIPTION OF THE PREFERRED EMBODIMENTS

Figure 1:
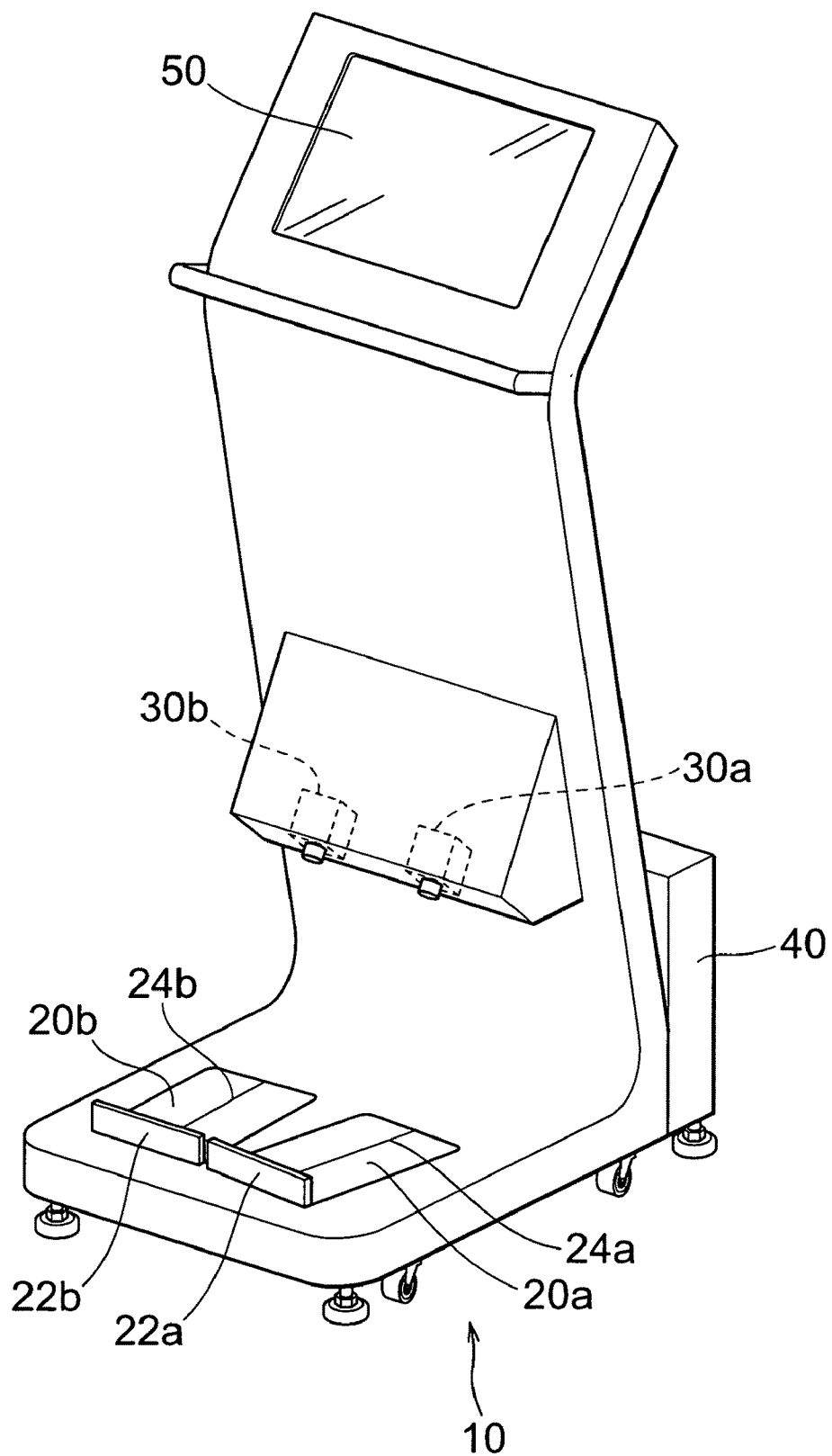
FIG. 1 is an appearance block diagram of a shoe or insole navigation system according to a preferred embodiment of the present invention.

FIG. 1 shows an appearance block diagram of a shoe or insole selection navigation system 10 according to a preferred embodiment of the present invention.

This system comprises foot sole pressure measuring sensors 20 (20a for right foot and 20b for left foot) for measuring foot sole pressure distributions of both feet of a subject standing upright on a measuring plane, foot image taking TV cameras 30 (30a for right foot and 30b for left foot) for taking images of both feet of the subject as the outer foot dimension measuring sensors, a processor 40 for acquiring pressure data from the foot sole pressure measuring sensors and image data from the foot image taking TV cameras and executing a shoe or insole selecting processing for selecting the subject's footcare shoe or insole, and a monitor screen 50 for displaying selection result of the shoe or insole selected by the processor 40 and guidance for the subject.

As for the foot sole pressure measuring sensors 20a and 20b in this preferred embodiment, pressure sensitive sensors of conductive rubber, 64×32 pieces of which are provided at 5 mm pitch for each foot, are used, thus permitting measurement of two-dimensional pressure distribution of foot sole pressure.

At the rear ends of the foot sole pressure measuring sensors 20a and 20b, heel stoppers 22 (22a for the right foot and 22b for the left foot) are provided for stabilizing heel positions to reference positions. Preferably, each surface of the heel stoppers 22a and 22b is formed of material, such as silicon material, having the same hardness as that of subcutaneous tissue of feet heel and the reference position is set at a position away from the surface by a predetermined length. This can minimize foot length measurement error caused by heel deformation when measurements of foot sizes (foot lengths) are conducted by identifying frontmost foot positions from the foot images taken by the foot image taking TV cameras with his/her heels fitted against the heel stoppers.

On the surfaces of the foot sole pressure measuring sensors 20a and 20b, center line indications 24 (24a for the right foot and 24b for the left foot) are displayed for aligning directions of the subject's feet.

In this preferred embodiment, in order to permit the foot sole pressure measurement by the subject in his/her natural posture, the foot sole pressure measuring sensors 20a and 20b are provided with an aperture angle of 10 degrees, with inclination angle where rear side is raised in consideration of gravity center balance during walking with shoes, and with a space of 15 cm between the both foot sole pressure measuring sensors.

To measure foot sole pressure distributions, the subject stands upright with his/her right foot and left foot stepped on the foot sole pressure measuring sensors 20a and 20b respectively, fits heel centers of his/her feet to the centers of the heel stoppers 22a and 22b respectively, and aligns his/her feet where the center line indications 24a and 24b are positioned between his/her forefinger and middle finger.

Furthermore, an adjustment element may be provided for adjusting the aperture angle and the inclination angle in accordance with subject's feet condition or shoes to be used.

As for the foot image taking TV cameras 30a and 30b in this preferred embodiment, CCD cameras are used, and images of the respective feet of the subject standing upright on the foot sole pressure measuring sensors 20a and 20b are taken from upper front direction.

Each of the foot images taken with the foot image taking TV cameras is subjected to image processing to be described later, whereby a frontmost foot position, an innermost foot position and outermost foot position in the image are identified, and a foot length is obtained based on a distance between the identified frontmost foot position in the image and the position of the heel stopper, and a foot width is obtained based on the identified innermost foot position and the outermost foot position in the image.

For obtaining the foot length and foot width as described above, information of vertical and horizontal lengths per unit pixel of the images taken by the foot image taking TV cameras 30a and 30b and relative positions of the heel stoppers 22a and 22b in the foot images are required. These pieces of information can be physically determined from settings of an optical system of the foot image taking TV cameras 30a and 30b. However, in this preferred embodiment, calibration of the vertical and horizontal lengths per unit pixel and the relative positions between the heel stoppers and the foot images can be performed by setting on the foot sole pressure measuring sensors 20a and 20b a calibration sheet where a lattice pattern of a uniform interval is drawn and then taking an image of this sheet with the foot image taking TV cameras 30a and 30b.

Subjects of this system possibly wear socks of different colors, and also a case is assumed where it is difficult to perform the image processing of identifying the foot part with necessary and sufficient contrast based on each of the images taken by the foot image taking TV cameras 30a and 30b. Accordingly, provided in this preferred embodiment are a resin seat colored in the white range and a resin seat colored in the black range which are to be fitted on the surface of the foot sole pressure measuring sensors 20a and 20b, thus permitting replacement therebetween in accordance with the color of subject's socks. This facilitates the image processing of detecting the outer foot positions based on the foot image, thereby performing more reliable measurement of the outer foot dimensions.

As for the processor 40 in this preferred embodiment, a personal computer is used. Any type of processors which acquires foot sole pressure data from the foot sole pressure measuring sensors, acquires foot images from the foot image taking TV cameras, performs predetermined computing processing, and displays a selection result of shoe or insole on the monitor screen may be used.

As for the monitor screen 50 in this preferred embodiment, a color LCD screen is used and pseudocolor display of the foot sole pressure distribution, which has been measured by the foot sole pressure measuring sensors, in correspondence with pressure values is provided.

Moreover, the monitor screen 50 is equipped with a touch screen, so that the subject can touch the screen to start the processing or to input subject-related information.

Figure 2:
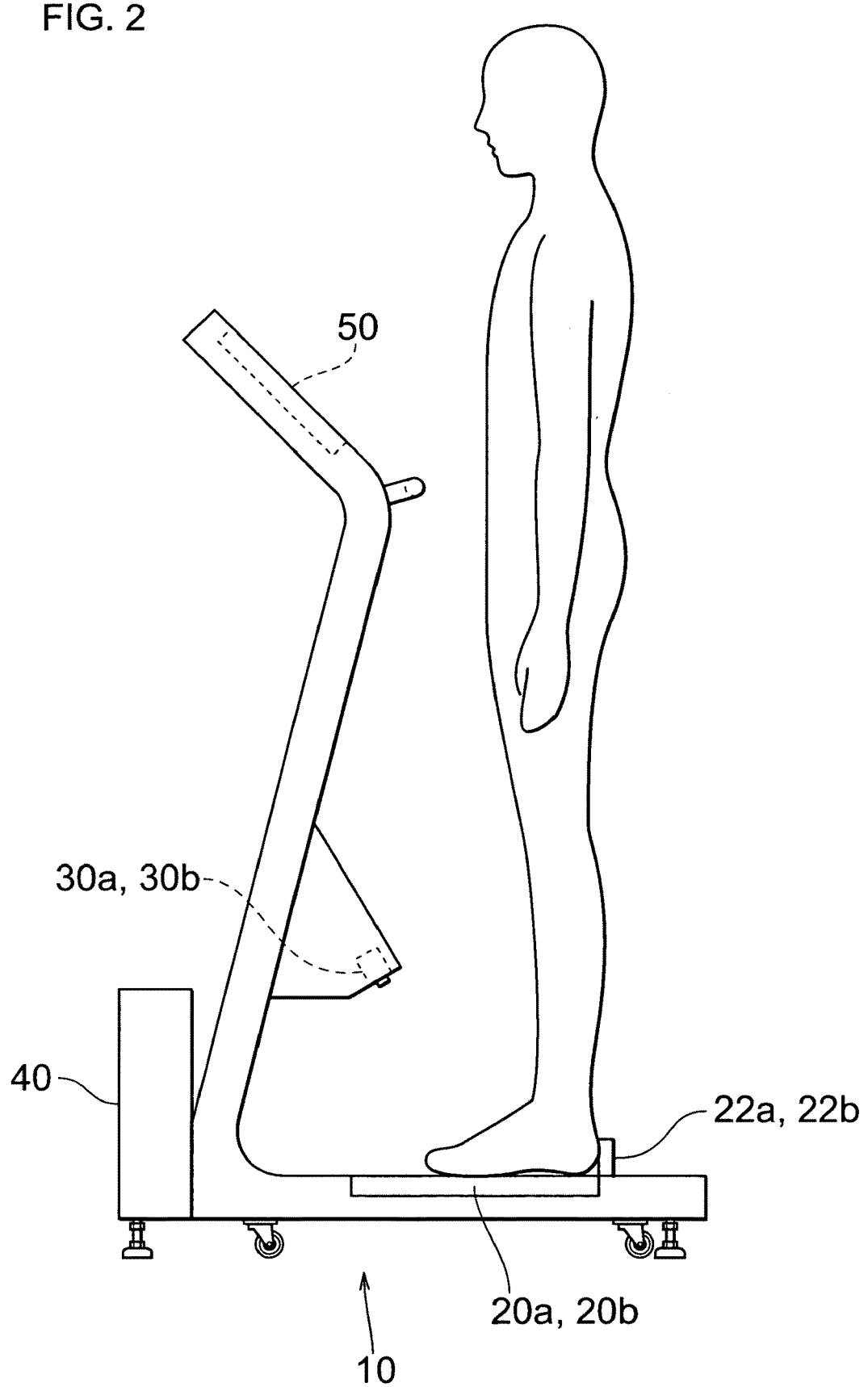
FIG. 2 shows use condition of the shoe or insole navigation system according to the preferred embodiment of the present invention.

FIG. 2 shows use condition of the shoe or insole selection navigation system according to the preferred embodiment of the present invention.

With this system, the subject stands upright with his/her feet stepped on the foot sole pressure measuring sensors 20a and 20b in accordance with the guidance displayed on the monitor screen 50, whereby the foot sole pressure measurement by the foot sole pressure measuring sensors and the outer foot dimensions measurement by the foot image taking TV cameras are performed simultaneously and a selection result of shoe or insole is displayed on the monitor screen 50.

Figure 3:
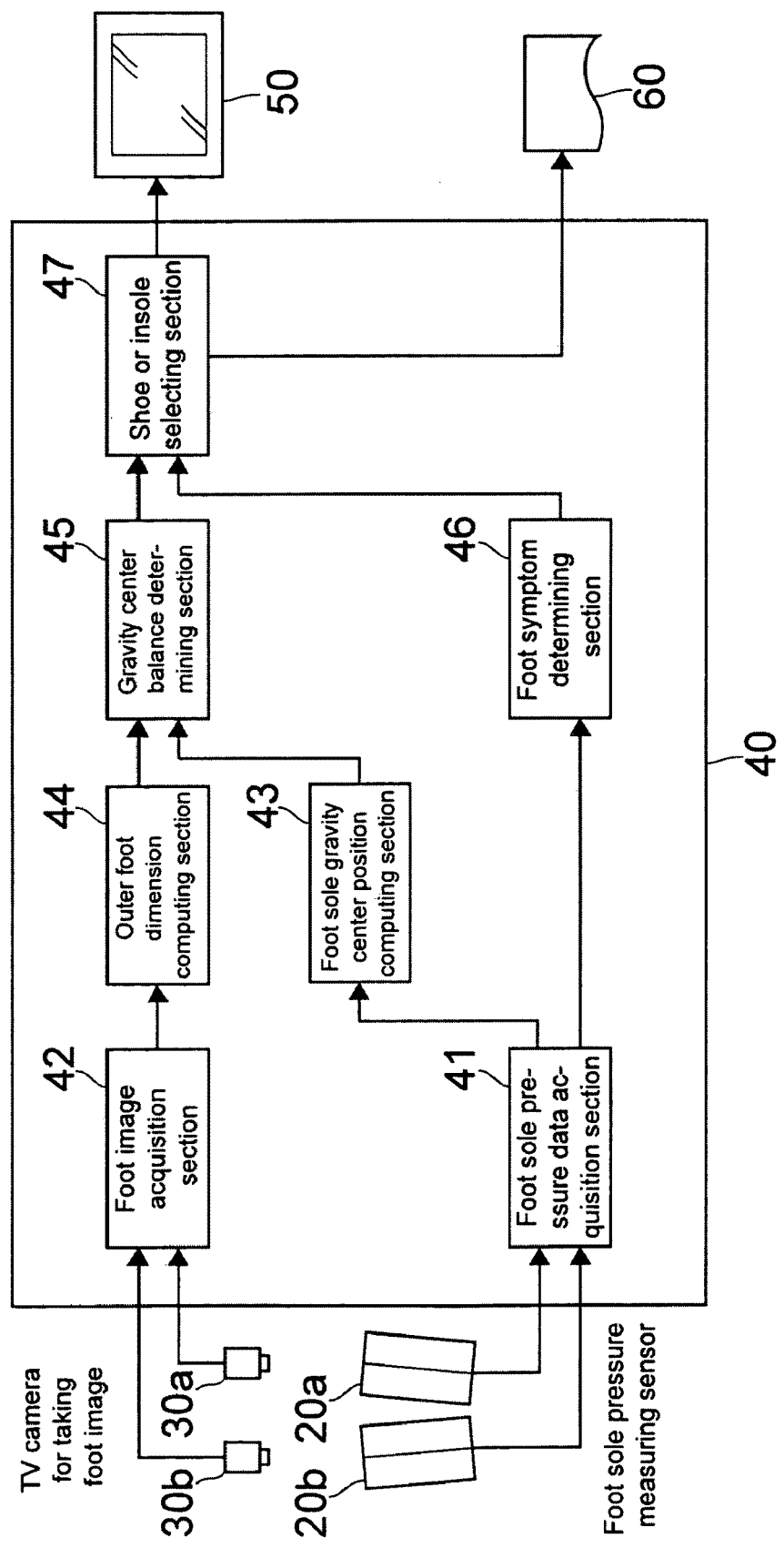
FIG. 3 is a block diagram of the shoe or insole navigation system according to the preferred embodiment of the present invention.

FIG. 3 shows block configuration of the processor 40 of the shoe or insole selection navigation system 10 according to the preferred embodiment of the present invention.

As shown in the figure, the processor 40 includes a foot sole pressure data acquisition section 41 for acquiring foot sole pressure data of each foot from the foot sole pressure measuring sensors 20a and 20b, a foot image acquisition section 42 for acquiring foot image of each foot from the foot image taking TV cameras 30a and 30b; a foot sole gravity center position computing section 43 for computing foot sole gravity center position of each foot based on the foot sole pressure data of each foot acquired by the foot sole pressure data acquisition section 41, an outer foot dimension computing section 44 for computing outer foot dimension of each foot based on the foot image of each foot acquired by the foot image acquisition section 42, a gravity center balance determining section 45 for computing bias in gravity center balance of each foot based on the foot sole gravity center position of each foot computed by the foot sole gravity center position computing section 43 and the outer foot dimension of each foot computed by the outer foot dimension computing section 44; a foot symptom determining section 46 for determining a foot symptom of each foot based on the foot sole pressure data of each foot acquired by the foot sole pressure data acquisition section 41; and a shoe or insole selecting section 47 for selecting a foot-care shoe or insole of each foot based on the bias in gravity center balance of each foot determined by the gravity center balance determining section 45 and the foot symptom of each foot determined by the foot symptom determining section 46.

The selection result of the shoe or insole selected by the shoe or insole selecting section 47 and foot diagnosis result are displayed on the monitor screen 50 to present them to the subject.

Moreover, this system also includes a function of creating subject's clinical record, and can record the selection result of shoe or insole and the foot diagnosis result on the subject's clinical record and can print the result by a printer 60 when needed.

Next, the information processing performed in the processor 40 will be explained in detail, illustrating a case where foot-care insoles are selected.

Figure 4:
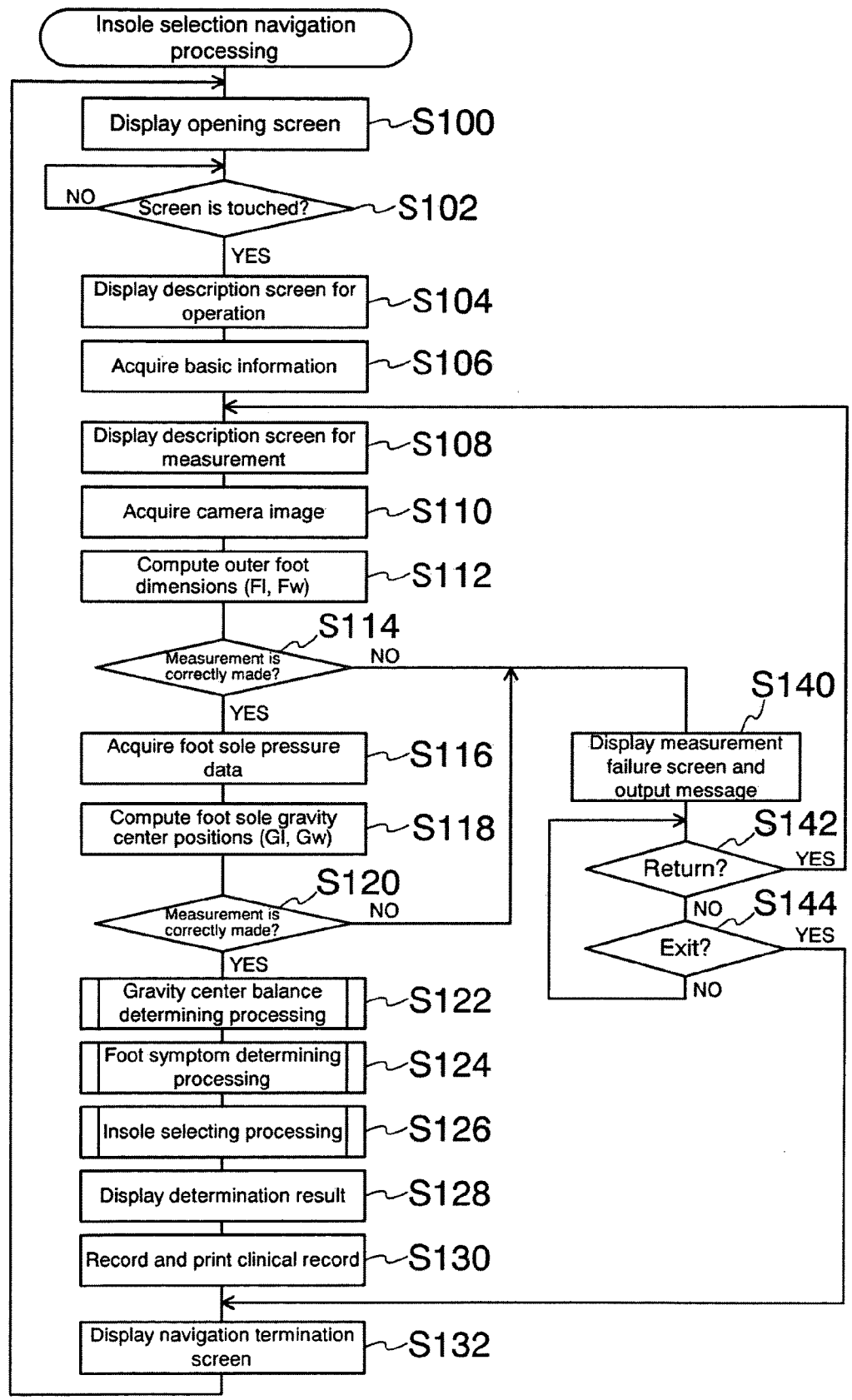
FIG. 4 is a flow chart showing procedures of an insole selection navigation processing according to the preferred embodiment of the present invention.

FIG. 4 shows procedures of insole selection navigation processing according to the preferred embodiment of the present invention.

During a standby mode, an opening screen describing a message "Touch the screen, and insole selection navigation will start." is displayed on the monitor screen 50 (S100).

If the screen touching is detected on the monitor screen 50 (S102), an operation instruction screen describing the operation of this system is displayed on the monitor screen 50 (S104).

Subsequently, a basic information acquisition screen is displayed, and basic information is acquired based on the touch position of the monitor screen (S106). In this preferred embodiment, in order to present recommended shoes at the time of displaying diagnosis result, subject's gender is acquired as the basic information. In addition, information such as age, height, desired shoe type and other information may be acquired.

Next, a measurement instruction screen describing how to step on the sensors, precautions at the measurement, and other information is displayed on the monitor screen 50, depending on the status (S108).

Subsequently, the subject is asked to step on the foot sole pressure measuring sensors in accordance with the measurement instruction screen displayed on the monitor screen, and after a certain period of time since a "measurement" button has been pressed or after a lapse of predetermined time, the foot image of both feet is acquired from the TV cameras 30a and 30b (S110). Image processing is performed on the acquired foot image of each foot to obtain outer foot dimension of each foot (foot length Fl, foot width Fw) (S112).

Figure 14:
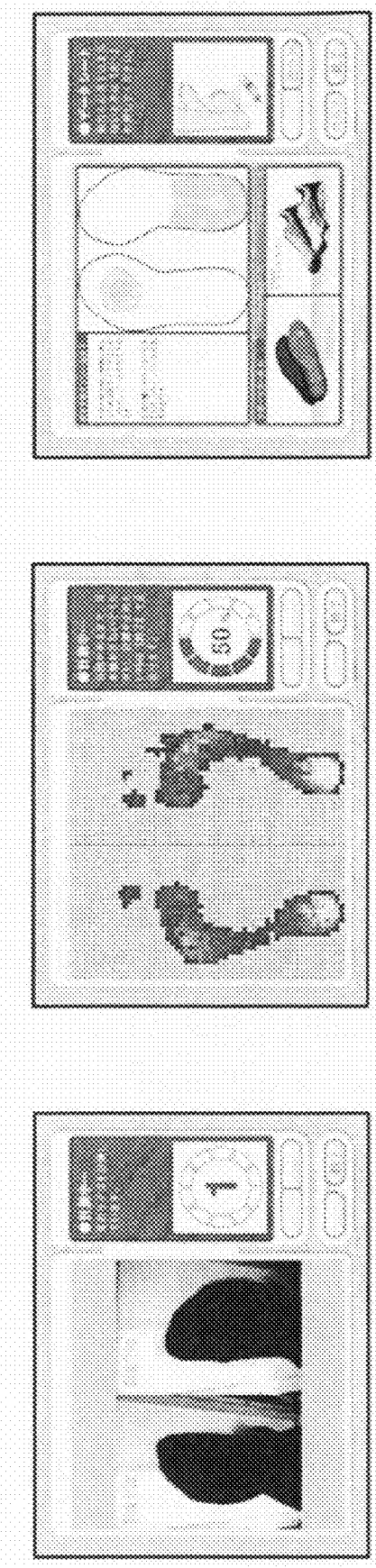
FIG. 14 is examples of an image displayed on a monitor screen in the insole selection navigation processing.

During the measurement of the outer foot dimension of each foot, the screen as shown in FIG. 14 (1) is displayed.

The image processing is performed on the acquired foot image of each foot, for example, in the following manner. First, after performing smoothing operation to remove noise content thereof, binarization operation is performed with an appropriate threshold value. Then based on the acquired binary image, a frontmost foot Y-coordinate Yf, an innermost foot X-coordinate Xi within a certain range of Y-axis from the frontmost foot Y-coordinate Yf, and an outermost foot X-coordinate Xo within the same are detected. Then based on the calibration data describe above, the foot length Fl is obtained from a difference between the frontmost foot Y-coordinate Yf and the rearmost foot Y-coordinate Yr which corresponds to each of the positions of the heel stoppers 22a and 22b, and the foot width Fw is obtained from a difference between the innermost foot X-coordinate Xi and the outermost foot X-coordinate Xo.

Note that the image processing is not limited to the above method. For example, for the foot image where smoothing operation is performed, a method in which the frontmost foot Y-coordinate Yf is detected by using a differential operator in Y-axis direction and the innermost foot X-coordinate Xi and the outermost foot X-coordinate Xo are detected by using a differential operator in X-axis direction, or a method in which the frontmost foot Y-coordinate Yf, innermost foot X-coordinate Xi, and outermost foot X-coordinate Xo are detected by tracing an edge of the foot image within a predetermined range can be used. Any method can be used which computes the outer foot dimensions from the foot image.

When the outer foot dimension (Fl and Fw) of each foot is properly measured (S114), two-dimensional foot sole pressure distribution data of each foot is acquired from the foot sole pressure measuring sensors 20a and 20b (S116).

During the measurement of the foot sole pressure data, a screen as shown in FIG. 14 (2) is displayed.

The measurement is performed for a period of ten seconds to obtain an average value of the foot sole pressure data excluding abnormal pressure values during this measurement.

Next, an moment computing is performed to the acquired foot sole pressure distribution data of each foot to compute the gravity center position (lengthwise gravity center position Gl and widthwise gravity center position Gw) of each foot on the basis of the outer foot position (rearmost foot Y-coordinate Yr and innermost foot X-coordinate Xi in this embodiment) of each foot detected by the above picture processing (S118). Defining that the foot sole pressure data of each foot on the basis of the rearmost foot Y-coordinate Yr and innermost foot X-coordinate Xi of each foot is P (i, j) (where i is Y axis coordinate and j is X axis coordinate), the foot sole gravity center position (Gl and Gw) of each foot is obtained by the following formula:

$$Gl = \Sigma i \Sigma j P(i,j) \times i / \Sigma i, j P(i,j),$$

$$Gw = \Sigma j \Sigma i P(i,j) \times i / \Sigma i, j P(i,j)$$

If the foot sole gravity center position (Gl and Gw) of each foot is properly measured (S120), gravity center balance determining processing is performed for each foot (S122). Details of the gravity center balance determination processing will be described later.

In addition, the foot symptom determining processing is performed to the acquired foot sole pressure distribution data of each foot (S124). It is determined here whether or not the subject has a front foot part problem including hallux valgus, a flat foot, or a high arch foot. Details of the foot symptom determining processing will be also described later.

Subsequently, the insole selecting processing is performed based on the determination result obtained through the gravity center balance determining processing and the determination result obtained through the foot symptom determining processing to select an insole which takes care of a foot problem of each foot of the subject by referring to an insole selection table to be described later (S126). Details of the insole selecting processing will be also described later.

Finally, the recommended insole of each foot selected through the insole selecting processing is displayed, and a determination result screen introducing recommended shoes is displayed on the monitor screen 50 (S128). The determination result is displayed as shown in FIG. 14 (3).

In addition, the determination result can be left on the subject's clinical record if he/she desires. The clinical record is displayed when a "Clinical record" button is pressed, the determination result is recorded on the clinical record when a "Save" button is pressed, and the clinical record is printed with the printer 60 when a "Print" button is pressed (S130).

When a series of processing is finished, a navigation termination screen is displayed (S132), and when an "Exit" button is pressed, the processing returns to the beginning to display the opening screen.

In a case where the outer foot dimension of each foot is not correctly measured in S114 or in a case where the foot sole gravity center position of each foot is not correctly measured in S120, a measurement failure message is displayed on the monitor screen (S140), and the processing returns to S108 to perform the measurement again when a "Return" button is pressed, and the processing proceeds to S132 to exit from the navigation when the "Exit" button is pressed.

Figure 5:
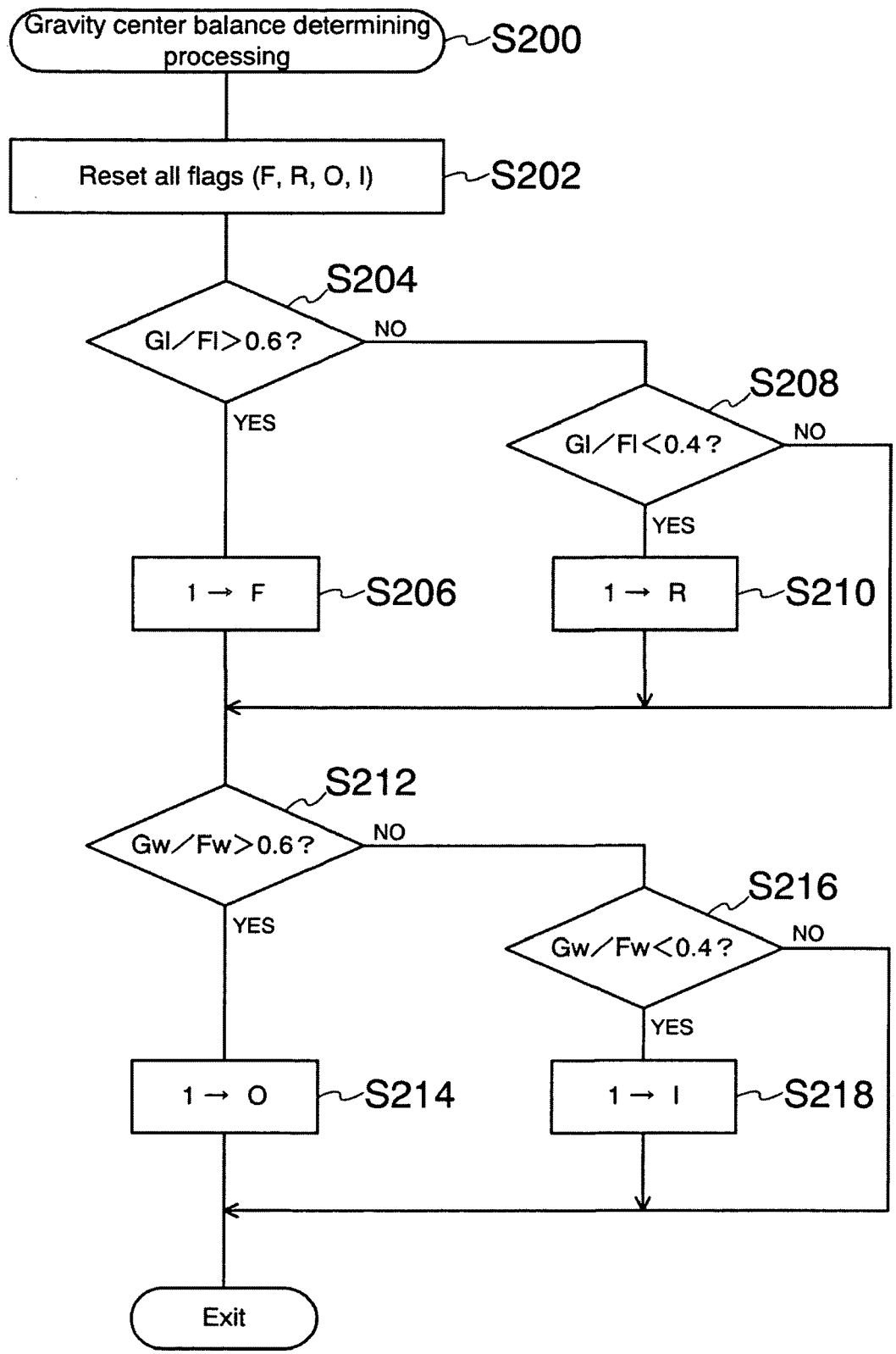
FIG. 5 is a flow chart showing procedures of gravity center balance determining processing in the insole selection navigation processing according to the preferred embodiment of the present invention.

FIG. 5 shows procedures of the gravity center balance determining processing.

The gravity center balance determining processing (S200) first resets all flags (front flag F, rear flag R, outside flag O, and inside flag I) which indicate bias in gravity center balance (S202).

If Gl/Fl exceeds 0.6, in other words, if the lengthwise gravity center position Gl exceeds 60% of the foot length Fl (S204), it is judged that the gravity center is biased to the front and then 1 is set for the front flag F (S206).

If Gl/Fl is less than 0.4, in other words, if the lengthwise gravity center position Gl is less than 40% of the foot length Fl (S208), it is judged that the gravity center is biased to the rear and then 1 is set for the rear flag R (S210).

If Gw/Fw exceeds 0.6, in other words, if the widthwise gravity center position Gw exceeds 60% of the foot width Fw (S212), it is judged that the gravity center is biased to the outside and then 1 is set for the outside flag O (S214).

If Gw/Fw is less than 0.4, in other words, if the widthwise gravity center position Gw is less than 40% of the foot width Fw (S216), it is judged that the gravity center is biased to the inside and then 1 is set for the inside flag I (S218).

Figure 7:
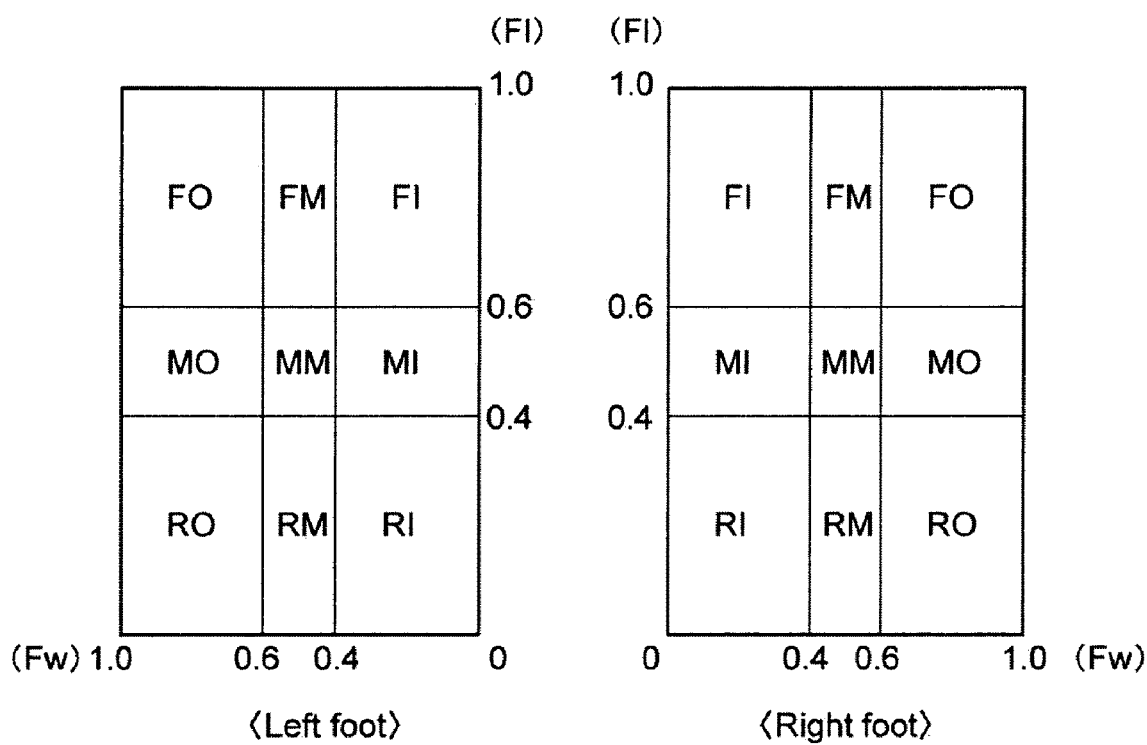
FIG. 7 shows determination division of the gravity center balance determining processing in the insole selection navigation processing according to the preferred embodiment of the present invention.

The bias in gravity center balance is judged as shown in FIG. 7 through the aforementioned gravity center balance determining processing (S200).

Specifically, the following judgments are made based on the foot sole gravity center positions with reference to the outer foot dimensions. When the foot sole gravity center positions fall within an MM range, it is judged that "No problem has been found". When they fall within an FM range, it is judged that "The gravity center is biased to the front side". When they fall within an RM range, it is judged that "The gravity center is biased to the rear side". When they fall within an MO range, it is judged that "The gravity center is biased to the outside". When they fall within an MI range, it is judged that "The gravity center is biased to the inside". When they fall within an FO range, it is judged that "The gravity center is biased to the front side and outside". When they fall within an FI range, it is judged that "The gravity center is biased to the front side and inside". When they fall within an RO range, it is judged that "The gravity center is biased to the rear side and outside". When they fall within an RI range, it is judged that "The gravity center is biased to the rear side and inside".

Figure 6:
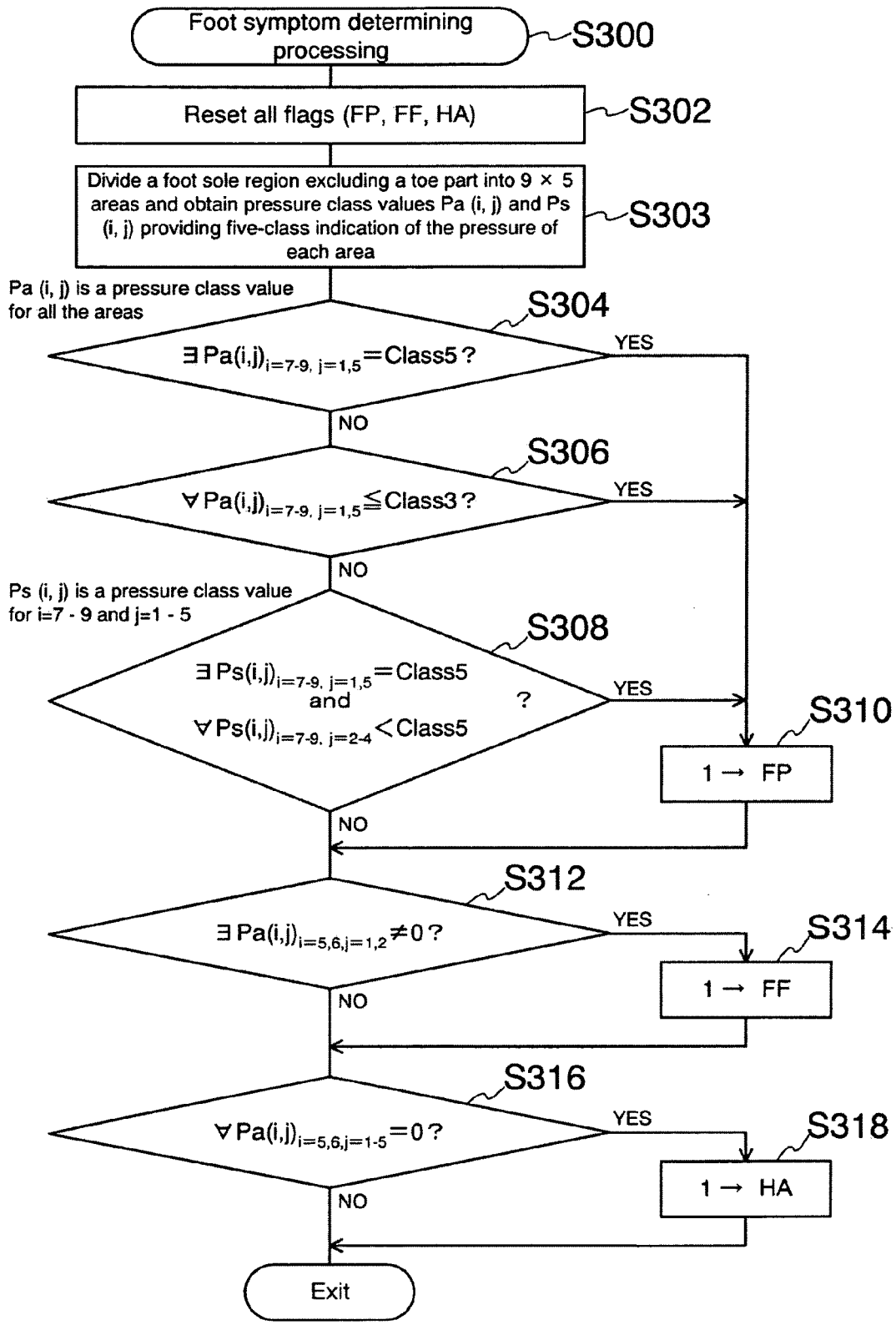
FIG. 6 is a flow chart showing procedures of foot symptom determining processing in the insole selection navigation processing according to the preferred embodiment of the present invention.

FIG. 6 shows procedures of the foot symptom determining processing.

The foot symptom determining processing (S300) first resets all flags (a front foot part problem flag FP, a flat foot flag FF, and a high arch flag HA) indicating foot problems (S302).

Next, a foot sole region excluding the foot part of the acquired foot sole pressure distribution data is divided into 9×5 areas, and then a pressure class value Pa (i, j) providing five-class indication of the pressure of each area based on a pressure range of all the areas and a pressure class value Ps (i, j) providing five-class indication of the pressure of each area based on a pressure range of the three rows on the front foot part areas are obtained (S303).

In the foot symptom determining processing, determination of a front foot part problem such as hallux valgus, determination of a flat foot, and determination of a high arch are performed based on the foot sole pressure class values Pa (i, j) and Ps (i, j) described above.

FIG. 8 shows the areas whose pressure class values are referenced upon the determinations (this is a case for the right foot).

In this preferred embodiment, i=9, 8 is a part unexceptionally corresponding to the front foot part, i=7 is a part corresponding to a gray zone of the front foot part and the middle foot part, i=6, 5 is a part unexceptionally corresponding to the middle foot part, i=4 is a part corresponding to a gray zone of the middle foot part and the rear foot part, and i=3, 2, 1 is a part unexceptionally corresponding to the rear foot part.

The front foot part problem is judged in the following three separate steps.

First, if it is detected that any of the pressure class values Pa (i, j) of i=7 to 9 and j=1, 5 corresponds to the pressure class 5 (maximum pressure) (S304), it is judged that the front foot part has a problem and 1 is set for the front foot part problem flag FP (S310).

Next, if it is detected that all of the pressure class values Pa (i, j) of i=7 to 9 and j=1, 5 correspond to the pressure class 3 or below (S306), it is judged that the front foot part has a problem and 1 is set for the front foot part problem flag FP (S310).

Finally, if it is detected that any of the pressure class values Ps (i, j) of i=7 to 9 and j=1, 5 corresponds to the pressure class 5 (maximum pressure) and that all of the pressure class values Ps (i, j) of i=7 to 9 and j=2 to 4 correspond to the pressure class less than 5 (S308), it is judged that the front foot part has a problem and 1 is set for the front foot part problem flag FP (S310).

As described above, the front foot part problems can be determined more accurately by changing determination condition in accordance with the pressure class of the front foot part.

For the flat foot, if any portion where the pressure is not 0 is detected among the pressure class values Pa (i, j) of i=5, 6 and j=1, 2 (S312), it is judged that the foot is a flat foot, and 1 is set for the flat foot flag FF (S314).

For the high arch, if it is detected that all the pressures of i=5, 6 and j=1 to 5 are 0 (S316), it is judged that the foot has a high arch, and 1 is set for the high arch flag HA (S318).

The insole selecting processing is performed by extracting a foot diagnosis message, an insole selection message, and a recommended insole type by referring to the insole selection table based on the setting condition of each of the flags (front flag F, rear flag R, inside flag I, and outside flag O) set through the gravity center balance determining processing and each of the flags (front foot part problem flag FP, flat foot flag FF, and high arch flag HA) set through the foot symptom determining processing.

Figure 9:
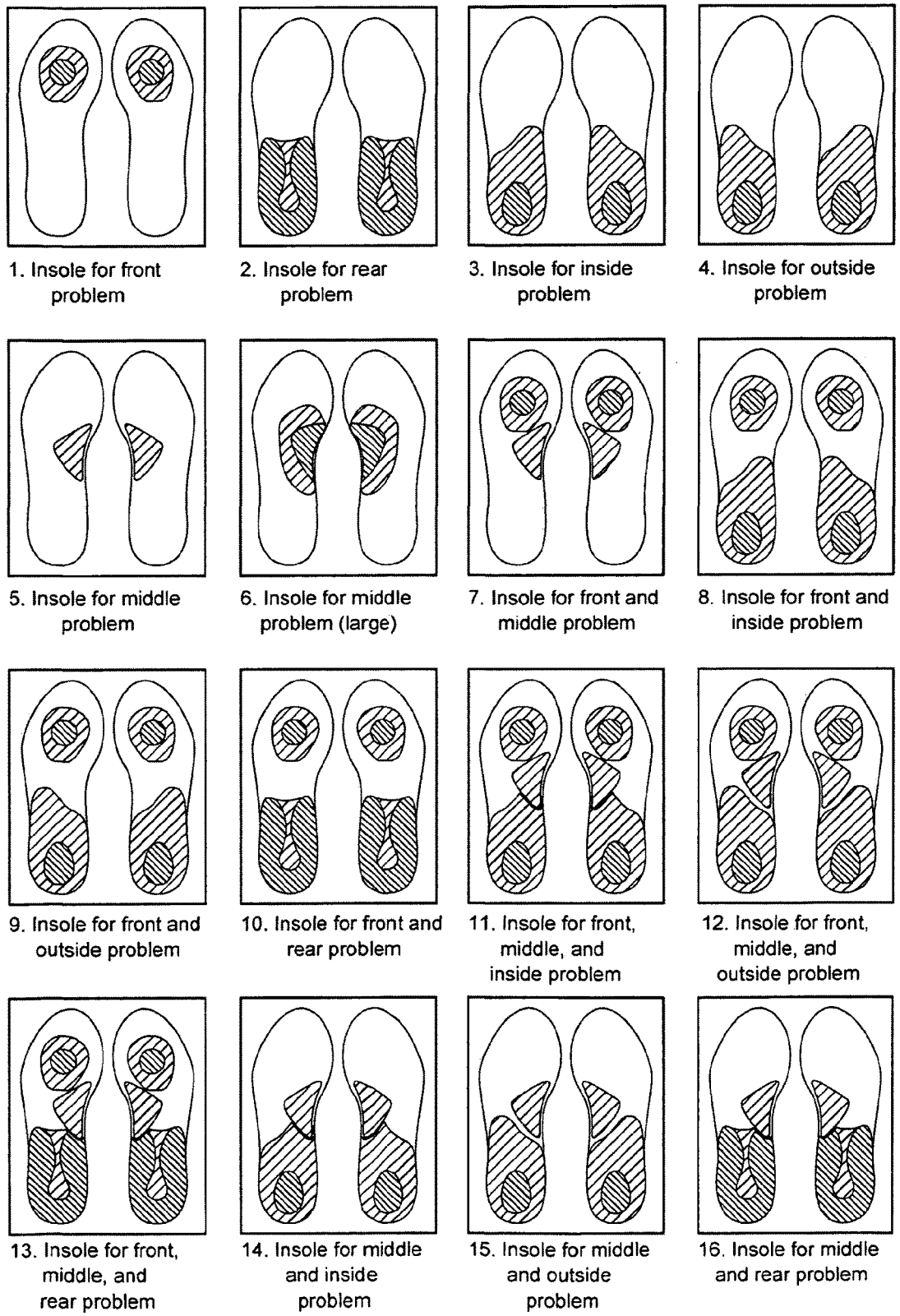
FIG. 9 shows examples of insoles to be selected through the insole selection navigation processing according to the preferred embodiment of the present invention.

FIG. 9 shows the insole types to be selected through this insole selecting processing.

The insole 1 includes a pad at the front foot part, and is mainly used for foot care in a case where the gravity center balance is biased to the front side or in a case where the front foot part has a problem.

The insole 2 includes a pad at the rear foot part, and is mainly used for foot care in a case where the gravity center balance is biased to the rear side.

The insole 3 includes a pad extending from the rear foot part toward the inside foot part, and is mainly used for foot care in a case where the gravity center balance is biased to the inside.

The insole 4 includes a pad extending from the rear foot part toward the outside foot part, and is mainly used for foot care in a case where the gravity center balance is biased to the outside.

The insole 5 includes a pad at the inside of the middle foot part, and is mainly used for foot care in the case of a mild flat foot.

The insole 6 has a reinforced version of the pad at the inside of the middle foot part, and is mainly used for foot care in a case of a severe flat foot.

The insole 7 combines the insole 1 and the insole 5 together, and is mainly used for foot care in a case where the foot is a flat foot or a high arch and also the front foot part has a problem or the gravity center balance is biased to the front side.

The insole 8 combines the insole 1 and the insole 3 together, and is mainly used for foot care in a case where the gravity center balance is biased to the front side and inside or in a case where the front foot part has a problem and the gravity center balance is biased to the inside.

The insole 9 combines the insole 1 and the insole 4 together, and is mainly used for foot care in a case where the gravity center balance is biased to the front side and outside or in a case where the front foot part has a problem and the gravity center balance is biased to the outside.

The insole 10 combines the insole 1 and the insole 2 together, and is mainly used for foot care in a case where the front foot part has a problem and the gravity center balance is biased to the rear side.

The insole 11 combines the insole 1, the insole 3, and the insole 5 together, and is mainly used for foot care in a case where the foot is a flat foot or a high arch and also the gravity center balance is biased to the front side and inside or in a case where the front foot part has a problem and also the gravity center balance is biased to the inside.

The insole 12 combines the insole 1, the insole 4, and the insole 5 together, and is mainly used for foot care in a case where the foot is a flat foot or a high arch and also the gravity center balance is biased to the front side and outside or in a case where the front foot part has a problem and also the gravity center balance is biased to the outside.

The insole 13 combines the insole 1, the insole 2, and the insole 5 together, and is mainly used for foot care in a case where the foot is a flat foot or a high arch, also the front foot part has a problem, and also the gravity center balance is biased to the rear side.

The insole 14 combines the insole 3 and the insole 5 together, and is mainly used for foot care in a case where the foot is a flat foot and also the gravity center balance is biased to the inside.

The insole 15 combines the insole 4 and the insole 5 together, and is mainly used for foot care in a case where the foot is a flat foot and also the gravity center balance is biased to the outside.

The insole 16 combines the insole 2 and the insole 5 together, and is mainly used for foot care in a case where the foot is a flat foot and also the gravity center balance is biased to the rear side.

FIGS. 10 and 11 show examples of the insole selection table for selecting the foot-care insoles based on the determination result of the gravity center balance determining processing and the determination result of the foot symptom determining processing.

The gravity center balance determining processing has a total of nine combinations (three combinations vertically× three combinations horizontally) as described above. The foot symptom determining processing has, as a combination of three symptoms, eight combinations, but considering that the combination of a flat foot and a high arch does not apply, the foot symptom determining processing actually has six combinations. Accordingly, 54 (9×6) determination combinations are created in total.

Regarding the 54 determination combinations, for the foot symptom determination result, insoles are selected based on an idea of a foot-care method employed by a general expert, and for the gravity center balance determination result, insoles are selected which operate in a direction more stabilizing the gravity center balance, in the insole selection tables in this embodiment.

When the determination result of the foot symptom determining processing conflicts with the determination result of the gravity center balance determining processing, priority is placed on the foot symptom improvement for the insole selection. When no conflict is found therebetween, the gravity center balance improvement is combined with the foot symptom improvement for the insole selection. In other words, when an insole based on the foot symptom determination serves as an insole based on the gravity center balance determination, or when an insole based on the gravity center balance determination prevents an advantage provided by an insole based on the foot symptom determination, the insole based on the gravity center balance determination is not selected.

From the insole selection tables shown in FIGS. 10 and 11, in correspondence with the setting condition of each of the determination flags (F, R, I, and O) set through the gravity center balance determining processing and the setting condition of each of the determination flags (FP, FF, and HA) set through the foot symptom determining processing, not only a recommended insole number but also a foot diagnosis message number and an insole selection message number are selected.

As a result, the foot diagnosis message is selected by referring to a foot diagnosis message table as shown in FIG. 12, the insole selection message is selected by referring to an insole selection message table as shown in FIG. 13, and the recommended insoles are displayed together with these messages on the monitor screen 50.

For the combination numbers 12, 17, 18, 30, 35, 36, 48, 53, and 54, two types of insoles are selected. They apply to a case where the front foot part has a problem and the gravity center is biased to the rear side, and correspond to the above described case that the foot symptom determination conflicts with the gravity center balance determination.

The insole selection messages in FIG. 13 serve to collectively display recommended types of insoles for a case where the front foot part has a problem and for a case where the front foot part has no problem, for simplification. In practice, however, the subject is asked to input information concerning whether or not the front foot part actually has a problem, such that a preferred type of insoles is displayed based on the input information.

In order to verify foot problem improvements by the insoles selected through the insole selection navigation processing as described above, for 38 subjects (20 males and 18 females) having a biased gravity center, a difference of gravity center fluctuation was measured between a case where the selected insole is used and for a case where the selected insole is not used. As a result, it was confirmed that the gravity center fluctuation was significantly improved especially for the left foot while the eyes are closed.

In addition, as a result of making a sensory evaluation survey on the 33 subjects (18 males and 15 females) of the subjects described above, concerning walking improvements during walking with the selected insoles actually fitted, not only the improvements on, for example, "fitness", "sense of stability", and "feeling in stand-up position" in static condition were highly rated, but also the improvements on, for example "walkability", "kicking during walking", etc. in dynamic condition were valued.

In this manner, it was confirmed that the foot-care insoles can be selected for the subject, who has a foot problem, through the above insole selection navigation processing, thereby the availability of this system is clarified.

Note that the insole selection tables and the insole type selected based on the tables, the way of determining a foot symptom, etc. in the above preferred embodiment are just examples and thus the present invention is not limited to them.

In the above preferred embodiment, it is described that the guidance and the determination result are displayed on the monitor screen 50 through the images. An audio message, BGM, etc. may be simultaneously outputted when needed.

In the above embodiment, it is described that the foot sole pressure distributions are measured through the foot sole pressure measuring sensors after measuring the outer foot dimensions through the foot image taking TV cameras. The foot sole pressure distribution may be measured first, or the outer foot dimensions and the foot sole pressure distribution may be measured simultaneously.

In the above preferred embodiment, the selection of insoles is described as an example, although the present invention is not limited thereto. The present invention is also applicable to selection of shoes by introducing a shoe selection table for selecting foot-care shoes based on the gravity center balance determination result and the foot problem determination result instead of the above insole selecting table. Any kind of foot-care goods, leg-care goods, leg clothes and the like for care of foot problems used along with shoes or insoles can be selected similarly.

In the above preferred embodiment, insole types are previously defined according to foot problem types, and insoles are selected from the insole types based on the gravity center balance determination result and the foot symptom determination result. In the insole selection table, fitting positions of problem-shooting pads may be presented corresponding to the gravity center balance determination result and the foot symptom determination result. This permits presentation of customer-made shoes or insoles to the subject.

In addition, pad thickness and shape may be presented in the insole selection table corresponding to the degrees of the bias in gravity center balance determined by the gravity center balance determining processing, the pressure values of a troubled part determined by the foot symptom determining processing, and other information. This permits presentation of customer-made shoes or insoles to the subject in accordance with a problem level.

The foot symptom determining section in the above preferred embodiment serves as a useful method even when separately used as a method of finding the front foot part problems including hallux valgus, a method of determining that the foot is a flat foot, or a method of determining that the foot is a high arch, thus providing particular advantage that a foot symptom can be determined adequately.

In the above preferred embodiment, it is described that, in the foot symptom determining section, the foot sole region excluding the toe part of the foot sole pressure distribution obtained by the foot sole measuring sensors is divided into a plurality of areas and the pressure class value of each of the areas is obtained to determine a foot abnormal symptom. The foot sole region including the toe part of the foot sole pressure distribution may be divided into a plurality of areas, and a foot abnormal symptom may be determined based on the pressure class value of each of the areas.

In the above preferred embodiment, it is described that the foot-care shoe or insole is selected by combining the gravity center balance determination and the foot symptom determination together. The foot-care shoe or insole may be selected by performing only the gravity center balance determination.

In the above preferred embodiment, it is described that as the outer foot dimension measuring sensor, the foot image taking TV cameras takes the images of the subject's feet with his/her heels adjusted to the heel stoppers from the front upper side, and then detects the frontmost, innermost and outermost positions of each foot to thereby measure the outer foot dimensions. Pressure sensitive sensors of a transparent material may be used as the foot sole pressure measuring sensors, the foot images may be taken with the TV cameras from the back side of the foot sole pressure measuring sensors, and then the frontmost, rearmost, innermost and outermost positions of each foot may be detected to thereby measure the outer foot dimensions.

In the above preferred embodiment, it is described that as the outer foot dimension measuring sensor, the two foot image taking TV cameras take the right and left foot images separately. Needless to say, a single super-high-resolution camera may be used to take the both foot images simultaneously.

In the above preferred embodiment, it is described that the outer foot dimensions measuring sensor measures the outer foot dimensions by subjecting the foot images taken by the foot image taking TV cameras to image processing, although the present invention is not limited to this. For example, a line light source and a line sensor may be oppositely provided in foot lengthwise and widthwise directions respectively, and the outer foot position may be detected based on a signal of the line sensor to thereby measure the foot length and foot width, or a mechanical device may be used to detect the outer foot position to thereby measure the foot length and foot width.

In the above preferred embodiment, the function of selecting the foot-care insole is described. For example, the function of presenting sizes of recommended shoes based on the outer foot dimensions measured by the outer foot dimension measuring means may be provided to simultaneously perform the selections of shoes and the selection of foot-care insoles.

In the above preferred embodiment, the foot sole pressure measuring sensors for right foot and left foot are separately provided in the measuring plane. A foot sole pressure measuring sensor formed integrally on the measuring plane may be provided, and the foot sole pressure distribution of each foot may be extracted from the acquired pressure distribution based on the positions of the heel stoppers and the directions of the reference lines.

In the above preferred embodiment, the foot sole pressure distribution is measured while the subject stands upright with his/her heel center adjusted to the heel stoppers and with the directions of his/her feet aligned along the reference lines, whereby permitting accurate determination of the bias in gravity center balance. It is also possible that, without providing the heel stoppers and the reference lines, the subject freely stands upright on the measuring plane of the foot sole pressure measuring sensors.

For example, the outer foot dimension measuring sensor may detect the front, rear, inside, and outside outer positions of each foot during the measurement of the foot sole pressure distribution by the foot sole pressure measuring sensor, a pressure distribution of each foot sole part may be extracted from the foot sole pressure distribution measured by the foot sole pressure measuring sensor based on the front, rear, inside, and outside outer positions of each foot detected by the outer foot dimension measuring sensor, the gravity center position of each foot may be computed based on the extracted pressure distribution of each foot sole part, and the bias in gravity center balance of each foot may be determined based on the computed gravity center position of each foot and the outer dimension of each foot measured by the outer foot dimension measuring sensor.

This permits the measurement of the foot sole pressure while the subject freely stands upright on the measuring plane, thus the bias in gravity center balance can be determined in less limited condition.

In addition, for example, the outer foot dimension measuring sensor may measure the outer dimension of each foot separately from the measurement of the foot sole pressure, front, rear, inside, and outside outer positions of each foot may be estimated based on the foot sole pressure distribution of each foot measured by the foot sole pressure measuring sensor, a pressure distribution of each foot sole part may be extracted from the foot sole pressure distribution of each foot measured by the foot sole pressure measuring sensor based on the estimated front, rear, inside, and outside outer positions of each foot, the gravity center position of each foot may be computed based on the extracted pressure distribution of each foot sole part, and the bias in gravity center balance of each foot may be determined based on the computed gravity center position of each foot and the outer dimension of each foot measured by the outer foot dimension measuring sensor.

The estimation of the outer positions of each foot may be performed, for example, by extracting the region where the pressure is detected for each foot from the foot sole pressure distribution of each foot measured by the foot sole pressure measuring sensor, comparing the front and rear pressure of the extracted region to thereby determine outermost position for the higher pressure as a reference position in a direction of front and rear, and comparing the inside and outside pressure of the extracted region to thereby determine outermost position for the higher pressure as a reference position in a direction of inside and outside, and setting an outer foot frame of each foot corresponding to the outer dimension of each foot measured by the outer foot dimension measuring sensor to the determined reference positions of each foot, whereby estimating the front, rear, inside and outside positions of each foot.

The comparison between the front and rear pressure and the comparison between the inside and outside pressure may be made by comparing the pressure of the two outermost parts or by comparing, for example, average values of the pressure on both sides from a foot sole center. Moreover, the reference positions in a direction of front and rear and in a direction of inside and outside may be determined based on which side the computed gravity center position of each foot is biased to.

The outer foot frame may be set corresponding to the determined front, rear, inside and outside reference positions of each foot with a predetermined offset by considering a part where the pressure is not detected. This offset may be modified depending on the subject's age, gender, feet size, or other condition.

Depending on the feet condition of the subject, the outer position of each foot may not be correctly estimated by the outer foot position estimating means. Accordingly, the outer foot frame set with reference to the foot sole pressure distribution of each foot may be displayed on the screen and the setting of the outer foot frame may be modified on the screen.

This permits the measurement of the foot sole pressure of each foot to be made separately from the measurement of the outer dimensions of each foot, while the subject freely stands upright on the measuring plane. Accordingly, in the measurement of the outer dimension of each foot as in the above preferred embodiment, even when the heel stoppers are provided and the foot sizes are measured based on the foot images, the subject can freely change a foot step in the measurement of the foot sole pressure distribution, thus the bias in gravity center balance can be determined in less limited condition.

In the above preferred embodiment, for the foot symptom determining section, the foot sole region is set based on the detected outer position of each foot. Accordingly, even when part of the foot sole has a defect part where load is not measured in the foot sole pressure distribution measured by the foot sole pressure measuring sensor, the pressure class values in each of the regions at the front foot part, the pressure class values in each of the regions at the inside part of middle foot part, and the pressure class values in each of the regions at the entire middle foot part can be correctly extracted, thus the front foot part problems including hallux valgus, a flat foot, or high arch can be determined accurately.

Also in this case, as described above, it is also possible that, without using the heel stoppers and the reference lines, the foot sole region may be set based on the front, rear, inside, and outside outer positions of each foot detected in the outer foot dimension measuring sensor, or the foot sole region may be set based on the front, rear, inside, and outside outer positions of each foot estimated by the outer foot dimension estimating sensor.

In the above preferred embodiment, it is described that the foot-care shoe or insole is finally selected in the shoe or insole selecting section. A gravity center fluctuation computing section may be provided which asks the subject to stand upright on the foot sole pressure measuring sensors while actually wearing the shoe or insole selected in the shoe or insole selecting section and then which confirms that the gravity center fluctuation while the subject wears the selected shoe or insole falls within a certain range by computing gravity center fluctuation parameters based on the change in the gravity center within the given period of time computed through the above gravity center computing. Alternatively; a gravity center fluctuation computing section may be provided which, after previously measuring the gravity center fluctuation while the subject wears a normal shoe or insole, confirms the degree of improvement on this gravity center fluctuation while the subject wears the selected shoe or insole.

In the preferred embodiment of the present invention, the foot sole pressure distribution can be acquired in real time from the foot sole pressure measuring sensor, and the change in the gravity center position can be computed in real time in the above foot sole gravity center position computing section. Accordingly, by computing the gravity center fluctuation parameters such as an outer circumferential area, a rectangle area, a root-mean-square value area, a length of total track, a length of unit track, and a track per unit area of a region where the gravity center has shifted, the gravity center fluctuation of each foot can be evaluated.

In addition, in the shoe or insole selecting section, a plurality of candidate foot-care shoes or insoles may be presented, the gravity center fluctuation for each of the presented insoles may be measured while the subject actually wears them, and the most preferable shoe or insole may be selected based on the measured gravity center fluctuations.

Figure 15:
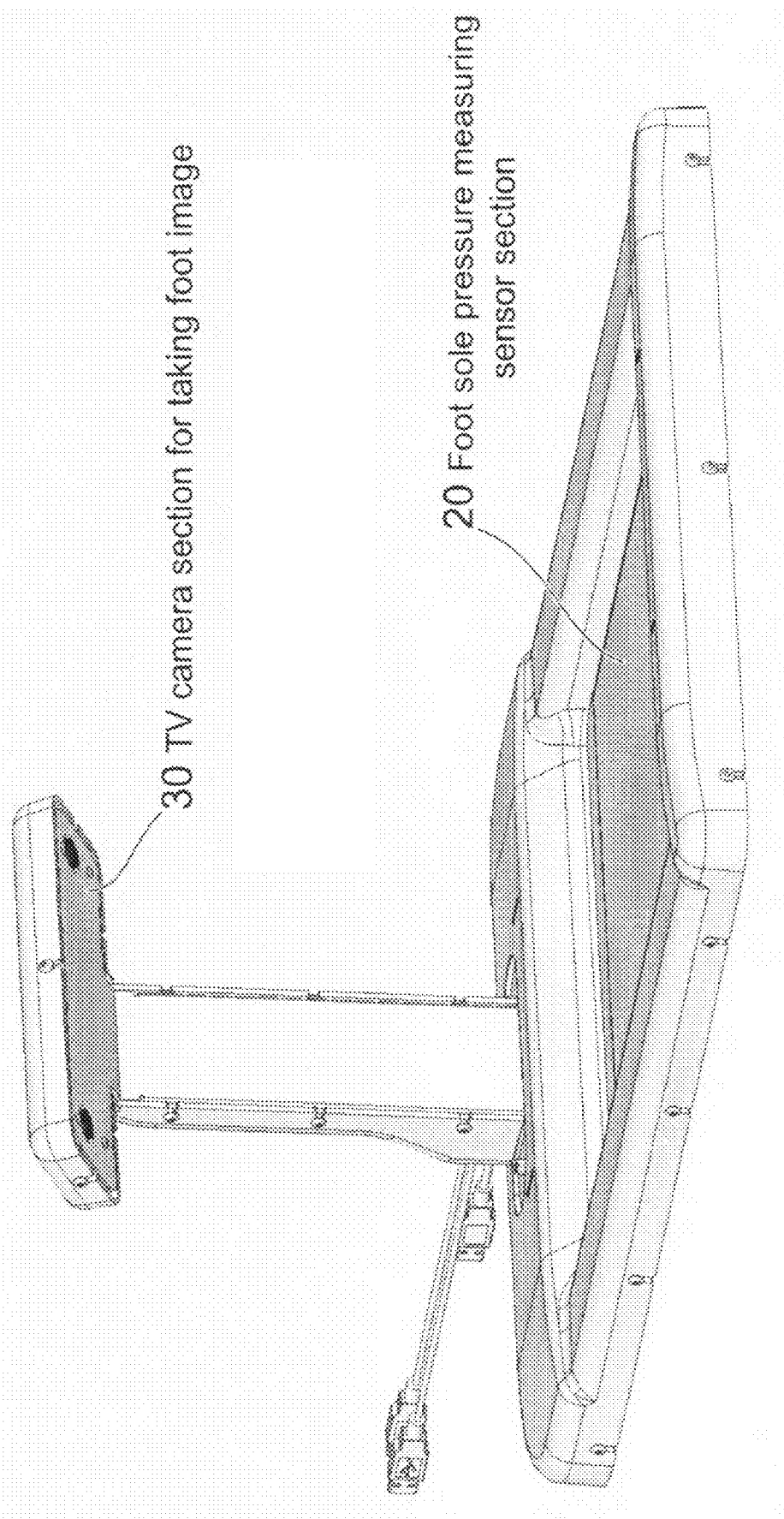
FIG. 15 is a appearance diagram of a measuring apparatus part of a shoe or insole navigation system according to another preferred embodiment of the present invention.

In the above preferred embodiment, the navigation system is described which includes in one housing the foot sole pressure measuring sensors for measuring the foot sole pressure, the image taking TV cameras for measuring the outer foot dimensions, the processor for executing the gravity center balance determining processing, the foot symptom determining processing and the foot-care shoe or insole selecting processing, and the monitor screen displaying the determination result. However, as shown in FIG. 15, the foot sole pressure measuring sensors and the foot image taking TV cameras may be included in a device main body and then connected to a general-purpose personal computer to execute the gravity center balance determining processing, the foot symptom determining processing, the foot-care shoe or insole selecting processing may be executed and display the determination result. Consequently, the device main body can be downsized, thereby permitting the gravity center balance determination, the foot symptom determination, or shoe or insole selection navigation to be easily performed even in a small-scale shop, home, and other places.

In the above preferred embodiment, the determination of the bias in gravity center balance and the determination of a foot symptom are performed to select foot-problem-care shoe or insole for each foot separately. A pelvis diagnosis section for diagnosing pelvis condition of the subject may be provided by combining the determination result for the right foot and the determination result for the left foot.

For example, a pelvis diagnosis table where pelvis diagnosis messages describing pelvis diagnosis information corresponding to combinations of the determination result of the bias in gravity center balance of the right foot and left foot are registered may be provided, and then the pelvis diagnosis message may be extracted by referring to the pelvis diagnosis table based on the flag indicating the bias in gravity center balance of the left foot and the right foot computed in the above gravity center balance determining section to display the extracted pelvis diagnosis message on the monitor screen.

The pelvis diagnosis messages to be displayed may include, for example, diagnosis messages for pelvis condition such as "It tends to be inclined forward.", "You have bow-legs.", and "You have knock-knees.", and may further include messages of advice information from a doctor for improving the determined pelvis condition such as "The pelvis will be possibly inclined forward. Exercise such as Pilates is recommended to develop the posture-supporting muscles" and "Load is likely to be imposed on the knees, and thus caution should be taken".

In addition, the pelvis diagnosis table may include modifying information for the selected shoe or insole corresponding to the combinations of the determination result of the bias in gravity center balance of the right foot and the left foot, and shoe or insole to be finally selected may be determined based on the modifying information registered in the pelvis diagnosis table.

A posture simulation displaying section for simulating the subject's posture and displaying it on the screen may be provided, based on the determination result of the bias in gravity center balance of the right foot and left foot.

For example, body information may be acquired from the subject, a standard three-dimensional human body model may be deformed based on the acquired body information to generate a three-dimensional human body model of the subject.

Next, based on the bias in gravity center balance of the right foot and left foot determined by the gravity center balance determining section, the subject's three-dimensional human body model may be deformed by referring to a posture deformation table defining how and which part of the three-dimensional human body model is deformed corresponding to the bias in gravity center balance of the right foot and left foot, to display the deformed subject's three-dimensional human body model on the screen.

In order to acquire the body information from the subject, for example, an image of the subject may be taken with a digital camera, the subject's feature points such as shoulders, waist, hip, fingers, feet may be extracted from the taken image by a image processing, and shoulder width, waist width, hip width, hand length, leg length, and other dimensions may be computed. For simplifying the image processing, an LED may be fitted on the feature points.

In the posture simulation displaying section, a moment computing section for computing the moment that works on the subject's body based on the bias in gravity center balance of both feet of the subject may be provided, to simulate the subject's posture and display it on the screen.

Figure 16:
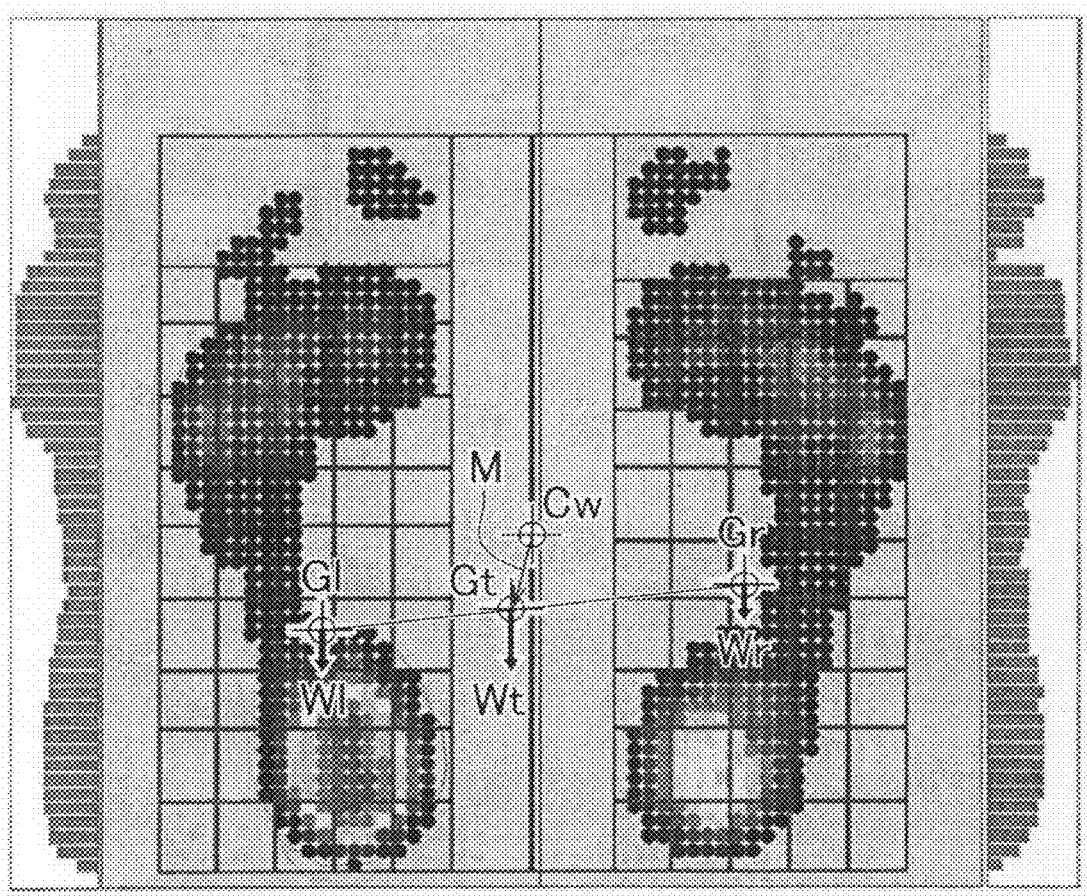
FIG. 16 is an explanatory diagram for posture simulation displaying function according to the preferred embodiment of the present invention.

The moment computing section may be configured to, as shown in FIG. 16, compute a total load of each foot Wr, Wl imposed on the gravity center position of each foot Gr, Gl computed by the gravity center position computing section based on the foot sole pressure distribution measured by the foot sole pressure measuring sensor, compute a total gravity center position Gt and total load Wt of the both feet based on the gravity center position of each foot Gr, Gl and the total load of each foot Wr, Wl, compute an ideal gravity center position Cw of the both feet based on the outer positions of the subject's both feet, and compute the moment M (vector) working on the subject's body based on the total gravity center Gt, the total load Wt, and the ideal gravity center position Cw.

Then, based on the moment M (vector) computed by the moment computing function, the subject's three-dimensional model may be deformed and displayed on the screen.

Consequently, the subject can specifically recognize how the moment working on the body due to the bias in gravity center balance of the feet influences the total posture.

As described above, according to the present invention, the navigation system is provided which can always determine the bias in gravity center balance of the foot sole accurately and select the foot-problem-care shoe or insole adequately.

Therefore, by setting the system of the present invention in a shop such as a shoe shop, a shoe purchaser can independently select shoes or insoles which fits his/her feet. In addition, the present invention may quantify the selection of shoe or insole, thereby the system of the present invention can be used as assistance to sales staff in a shoe shop.

The present invention includes the selecting section to thereby provide a foot-care shoe or insole selection navigation system which cares a foot problem of the subject. The sections of the present invention other than the selecting section thereof can be also used as a diagnosis device for diagnosing condition of the subject's feet.

Specifically, including the foot sole pressure measuring sensor, the outer foot dimension measuring sensor, the gravity center position computing section, and the gravity center balance determining section can provide a foot diagnosis device which can always diagnose the bias in gravity center balance of the foot sole accurately.

In addition, for a foot problem found by the determining function of the present invention, a function of suggesting stretching exercise or rehabilitation exercise, presenting instructions about improvements on one's dietary life, suggesting intake of a supplement, or suggesting clothes may be included, thereby providing a living improvement support system.

Additionally life style data base for managing individual life style may be included. Accordingly, in corporation with various systems that present products such as foot-care goods, sport goods, esthetic equipment, food stuff, clothes, medicines and supplements, and service such as medical cares, educations, sports, beauty treatments and travels, the system of the present invention may support all of food, clothing and shelter, starting with the foot-care support and can be developed as an integrated support system which suggest an optimal life style recipe to individuals.

The present invention is not limited to the preferred embodiment described above, and the components described in the preferred embodiments may be replaced as appropriate, a new component may be added, and part of the components may be deleted, as far as providing the advantage of the present invention.

What is claimed is:

1. A shoe or insole fitting navigation system including:
   a foot sole pressure measuring sensor configured to measure a foot sole pressure distribution for each foot of a subject standing upright on a measuring plane with one foot having a load bearing defect part where the pressure is measured as zero;
   an outer foot dimension measuring sensor configured to measure an outer dimension of each foot of the subject by detecting an outer position of each foot, wherein the outer dimension of each foot and foot sole pressure distributions of the subject are capable of being measured simultaneously;
   a gravity center position computing section configured to compute a gravity center position of each foot from the foot sole pressure distribution of each foot measured by the foot sole pressure measuring sensor, and the outer position of each foot measured by the outer foot dimension measuring sensor, so as correctly to determine the gravity center position of the sole of each foot;
   a gravity center balance determining section configured to determine a bias in a gravity center balance of each foot, which represents how much the gravity center position of each foot is biased from a central portion of the respective foot sole, based on the gravity center position of each foot computed by the gravity center position computing section and the outer dimension of each foot measured by the outer foot dimension measuring sensor; and
   a selecting section configured to select a shoe or insole for each foot based on the bias in gravity center balance of each foot determined by the gravity center balance determining section.

2. The shoe or insole fitting navigation system according to claim 1, wherein the outer foot dimension measuring sensor includes:
   an image taking TV camera configured to take a foot image of each foot; and
   an image processing section configured to compute a foot length and a foot width by detecting an outer position of each foot from the foot image of each foot taken by the image taking TV camera.

3. The shoe or insole fitting navigation system according to claim 1, further including a foot symptom determining section configured to determine whether an abnormal foot symptom exists in each foot, by dividing the foot sole pressure distribution of each foot measured by the foot sole pressure measuring sensor into a plurality of regions, computing pressure class values in these divided regions, and comparing the computed pressure class values with a previously defined combination condition of pressure class values,
   wherein the selecting section selects a foot-care shoe or insole based on the bias in gravity center balance of each foot determined by the gravity center balance determining section and any foot symptom of each foot determined by the foot symptom determining section.

4. The shoe or insole fitting navigation system according to claim 3, wherein the selecting section is configured to select a shoe or insole by combining the selection of the shoe or insole based on the bias in gravity center balance with the selection of shoe or insole based on the foot symptom, and wherein when the selection based on the bias in gravity center balance conflicts with the selection based on the foot symptom, priority is given to the selection based on the foot symptom.

5. The shoe or insole fitting navigation system according to claim 3, wherein the foot symptom determining section is configured to divide a foot sole region, excluding a toe part, into the plurality of regions and compute first pressure class values in these divided regions based on a pressure range of all regions and second pressure class values in these divided regions based on a pressure range of three rows of regions on a front foot part, to determine that:
   a front foot part problem including a hallux valgus exists if any of the following conditions are detected
      any of the computed first pressure class values in an outside part of the front foot part are at a maximum value of the first pressure class,
      all of the computed first pressure class values in an outside part of the front foot part are at or below a middle value of the first pressure class, and
      any of the computed second pressure class values in the outside part of the front foot part are at a maximum value of the second class and all of the computed second pressure class values in an inside part of the front foot part are less than the maximum value of the second pressure class, a flat foot exists if it is detected that any of the computed first pressure class values in an inside part of a middle foot part is not a minimum value of the first pressure class, and a high arch exists if it is detected that all of the computed first pressure class values in the entire middle foot part are a minimum value of the first pressure class.

6. The shoe or insole fitting navigation system according to claim 1, wherein the selecting section is configured to present an alignment method of one or more pads to a shoe or insole.

7. The shoe or insole fitting navigation system according to claim 1, further including a gravity center fluctuation section configured to check a suitability of the selected shoe or insole by having the subject wear the selected shoe or insole on a respective foot and stand on the foot sole pressure measuring sensor to confirm that a gravity center fluctuation falls within a predetermined range by computing gravity center fluctuation data based on a change in the gravity center position of the respective foot during a given period of time.

8. The shoe or insole fitting navigation system according to claim 1, further including a pelvis diagnosis section configured to diagnose a pelvis condition of the subject by combining the determination result of the bias in gravity center balance of the left foot and the right foot, wherein a related pelvis diagnosis message is extracted based on the determination results of the bias in gravity center balance of both feet determined by the gravity center balance determining section by referring to a pelvis diagnosis table in which pelvis diagnosis messages describing pelvis diagnosis information corresponding to the combination of the bias in gravity center balance of the left foot and that of right foot are registered, to display the extracted pelvis diagnosis message on a screen.

9. The shoe or insole fitting navigation system according to claim 1, further including a posture simulation displaying section configured to display a posture simulation by generating a three-dimensional human body model of the subject based on body information of the subject, deforming the generated three-dimensional human body model based on the bias in gravity center balance of both feet determined by the gravity center balance determining section, and displaying the deformed three-dimensional human body model on a screen.

10. The shoe or insole fitting navigation system according to claim 9, wherein the posture simulation displaying section includes a moment computing section which is configured to:

compute a total load imposed on the gravity center position of each foot based on the foot sole pressure distribution of each foot measured by the foot sole pressure measuring sensor;

compute a total gravity center position and a total load of both feet based on the computed gravity center positions each foot and the computed total load of each foot;

compute an ideal gravity center position of both feet based on the outer positions of both feet of the subject; and compute a moment working on the body of the subject based on the computed total gravity center position, the computed total load of both feet, and the computed ideal gravity center position, to deform the generated subject's three-dimensional human body model, and display the deformed three-dimensional human body model on the screen.

11. The shoe or insole fitting navigation system according to claim 1, wherein the gravity center balance determining section is configured to judge that:

the gravity center is biased to a front of the foot if a computed lengthwise gravity center position exceeds 60% of the foot length measured by the outer dimension measuring sensor, the gravity center is biased to a rear of the foot if the computed lengthwise gravity center position is less than 40% of the foot length measured by the outer dimension measuring sensor, the gravity center is biased to an outside of the foot if a computed widthwise gravity center position exceeds 60% of a foot width measured by the outer dimension measuring sensor, and the gravity center is biased to an inside of the foot if the computed lengthwise gravity center position is less than 40% of the foot width measured by the outer dimension measuring sensor.

12. A shoe or insole fitting navigation system including:

a foot sole pressure measuring sensor configured to measure a pressure distribution of each foot of a subject standing upright on a measuring plane with one foot having a load bearing defect part where the pressure is measured as zero;

an outer foot dimension measuring sensor configured to measure an outer dimension of each foot of the subject, wherein the outer dimension of each foot and foot sole pressure distributions of the subject are capable of being measured simultaneously, and further including an outer foot position estimating section configured to estimate an outer position of each foot by extracting a region where the pressure is detected for each foot from the foot sole pressure distribution measured by the foot sole pressure measuring sensor, determining reference positions in a front, rear, inside and outside of each foot based on the foot sole pressure distribution of the extracted region of each foot, and setting an outer foot frame of each foot corresponding to the outer dimension of each foot measured by the outer foot dimension measuring sensor to the determined reference positions of each foot;

a gravity center position computing section configured to compute a gravity center position of each foot from the foot sole pressure distribution measured by the foot sole pressure measuring sensor, and the outer position of each foot estimated by the outer foot position estimating section, so as correctly to determine the gravity center position of the sole of each foot;

a gravity center balance determining section configured to determine a bias in a gravity center balance of each foot, which represents how much the gravity center position is biased from central portion of foot sole, based on the gravity center position of each foot computed by the gravity center position computing section and the outer dimension of each foot measured by the outer foot dimension measuring sensor; and a selecting section configured to select a shoe or insole based on the bias in gravity center balance of each foot determined by the gravity center balance determining section.

13. The shoe or insole fitting navigation system according to claim 12, wherein the outer foot dimension measuring sensor includes:

an image taking TV camera configured to take a foot image of each foot; and an image processing section configured to compute a foot length and a foot width by detecting an outer position of each foot from the foot image of each foot taken by the image taking TV camera.

14. The shoe or insole fitting navigation system according to claim 12, further including a foot symptom determining section configured to determine whether an abnormal foot symptom exists in each foot, by dividing the foot sole pressure distribution of each foot measured by the foot sole pressure measuring sensor into a plurality of regions, computing pressure class values in these divided regions, and comparing the computed pressure class values with a previously defined combination condition of pressure class values, wherein the selecting section selects a foot-care shoe or insole based on the bias in gravity center balance of each foot determined by the gravity center balance determining section and on any foot symptom of each foot determined by the foot system determining section.

15. The shoe or insole fitting navigation system according to claim 14, wherein the foot symptom determining section is configured to divide a foot sole region, excluding a toe part, into the plurality of regions and compute first pressure class values in these divided regions based on a pressure range of all regions and second pressure class values in these divided regions based on a pressure range of three rows of regions on a front foot part, to determine that:

a front foot part problem including a hallux valgus exists if any of the following conditions are detected
  any of the computed first pressure class values in an outside part of the front foot part are at a maximum value of the first pressure class,
  all of the computed first pressure class values in an outside part of the front foot part are at or below a middle value of the first pressure class, and
  any of the computed second pressure class values in the outside part of the front foot part are at a maximum value of the second class and all of the computed second pressure class values in an inside part of the front foot part are less than the maximum value of the second pressure class,
a flat foot exists if it is detected that any of the computed first pressure class values in an inside part of a middle foot part is not a minimum value of the first pressure class, and
a high arch exists if it is detected that all of the computed first pressure class values in the entire middle foot part are a minimum value of the first pressure class.

16. The shoe or insole fitting navigation system according to claim 14, wherein the selecting section is configured to select a shoe or insole by combining, the selection of shoe or insole based on the bias in gravity center balance with the selection of shoe or insole based on the foot symptom, and wherein when the selection based on the bias in gravity center balance conflicts with the selection based on the foot symptom, priority is given to the selection based on the foot symptom.

17. The shoe or insole fitting navigation system according to claim 12, wherein the selecting section is configured to present an alignment method of one or more pads to a shoe or insole.

18. The shoe or insole fitting navigation system according to claim 12, further including a gravity center fluctuation checking section configured to check a suitability of the selected shoe or insole by having the subject wear the selected shoe or insole and stand on the foot sole pressure measuring sensor to confirm that a gravity center fluctuation falls within a predetermined range by computing gravity center fluctuation data based on a change in the gravity center position of each foot during a given period of time.

19. The shoe or insole fitting navigation system according to claim 12, further including:
  a pelvis diagnosis section configured to diagnose a pelvis condition of the subject by combining the determination result of the bias in gravity center balance of the left foot and the right foot, wherein
  a related pelvis diagnosis message is extracted based on the combined determination results of the bias in gravity center balance of both feet determined by the gravity center balance determining section by referring to a pelvis diagnosis table in which pelvis diagnosis messages describing pelvis diagnosis information corresponding to the combination of the bias in gravity center balance of the left foot and that of right foot are registered, to display the extracted pelvis diagnosis message on a screen.

20. The shoe or insole fitting navigation system according to claim 12, further including a posture simulation displaying section configured to display a posture simulation by generating a three-dimensional human body model of the subject based on body information of the subject, deforming the generated three-dimensional human body model based on the bias in gravity center balance of both feet determined by the gravity center balance determining section, and displaying the deformed three-dimensional human body model on a screen.

21. The shoe or insole fitting navigation system according to claim 20, wherein the posture simulation displaying section includes a moment computing section which is configured to:
  compute a total load imposed on the gravity center position of each foot based on the foot sole pressure distribution of each foot measured by the foot sole pressure measuring sensor;
  compute a total gravity center position and a total load of both feet based on the computed gravity center positions of each foot and the computed total load of each foot;
  compute an ideal gravity center position of both feet based on the outer positions of both feet of the subject; and
  compute a moment working on the body of the subject based on the computed total gravity center position, the computed total load of both feet, and the computed ideal gravity center position to deform the generated subject's three-dimensional human body model, and
  display the deformed three-dimensional human body model on the screen.

22. The shoe or insole fitting navigation system according to claim 12, wherein the gravity center balance determining section is configured to judge whether:
  the gravity center is biased to the front if a computed lengthwise gravity center position exceeds 60% of a foot length measured by the outer dimension measuring sensor,
  the gravity center is biased to the rear if the computed lengthwise gravity center position is less than 40% of the foot length measured by the outer dimension measuring sensor,
  the gravity center is biased to the outside if a computed widthwise gravity center position exceeds 60% of a foot width measured by the outer dimension measuring sensor, and
  the gravity center is biased to the inside if the computed lengthwise gravity center position is less than 40% of the foot width measured by the outer dimension measuring sensor.

* * * * *